United States Patent [19]

Kakimoto et al.

[11] Patent Number: 4,875,909

[45] Date of Patent: Oct. 24, 1989

[54] METHOD FOR RECOVERY OF ETHYLENE OXIDE

[75] Inventors: Yukihiko Kakimoto; Masayuki Sawada; Yoshiaki Kajimoto, all of Yokohama; Isamu Kiguchi, deceased, late of Zushi, all of Japan, by Kuniko Kiguchi, legal representative

[73] Assignees: Nippon Shokubai Kasaku Kogyo Co., Ltd., Osaka, Japan; Atochem, Paris, France

[21] Appl. No.: 127,488

[22] Filed: Dec. 1, 1987

Related U.S. Application Data

[63] Continuation-in-part of Ser. No. 878,113, Jun. 25, 1986, abandoned.

[30] Foreign Application Priority Data

Jun. 27, 1985 [JP] Japan .................................. 60-139175
Jul. 4, 1985 [JP] Japan .................................. 60-145850

[51] Int. Cl.$^4$ .............................................. B01D 53/14
[52] U.S. Cl. ............................................. 55/40; 55/48; 55/50; 55/51; 549/538
[58] Field of Search .................................. 55/40, 48–51, 55/68; 159/2.1; 203/14, 22, 23, 26, 42, 71, 73, 78–80, 84, 85, 88, 92, 93, 95–97, DIG. 4; 549/538, 541

[56] References Cited

U.S. PATENT DOCUMENTS

| | | | |
|---|---|---|---|
| 2,806,552 | 9/1957 | Koble | 55/51 X |
| 3,165,539 | 1/1965 | Lutz | 55/51 X |
| 3,174,262 | 3/1965 | Lutz | 55/51 X |
| 3,217,466 | 11/1965 | Bogart . | |
| 3,357,900 | 12/1967 | Snell | 203/88 X |
| 3,729,899 | 5/1973 | Cunningham et al. | 55/51 X |
| 3,766,714 | 10/1973 | Cunningham et al. | 55/51 X |
| 4,028,070 | 6/1977 | Uchii et al. . | |
| 4,033,617 | 7/1977 | Cocuzza et al. | 55/50 X |
| 4,137,129 | 1/1979 | Bjorklund | 203/88 X |
| 4,184,855 | 1/1980 | Butwell et al. | 55/49 X |
| 4,294,590 | 10/1981 | Linde et al. | 55/49 X |
| 4,378,977 | 4/1983 | Linde et al. | 55/49 X |
| 4,422,903 | 12/1983 | Messick et al. | 203/DIG. 13 |
| 4,469,492 | 9/1984 | Laganá et al. | 55/51 X |
| 4,589,889 | 5/1986 | Spencer | 55/51 X |

FOREIGN PATENT DOCUMENTS

121607 7/1946 Australia ............................... 55/51
2359499 6/1974 Fed. Rep. of Germany .

Primary Examiner—Robert Spitzer
Attorney, Agent, or Firm—Omri M. Behr

[57] ABSTRACT

In the recovery of ethylene oxide from the gas resulting from catalytic gas-phase oxidation of ethylene with a molecular oxygen-containing gas and consequently containing ethylene oxide, a method which comprises subjecting the bottom liquid of an ethylene oxide stripper to a flashing treatment thereby separating the bottom liquid into a vapor-phase part and a liquid-phase part, introducing the vapor-phase part in a compressed state into the bottom of the ethylene oxide stripper, and circulating the liquid-phase part to the absorber. The liquid-phase part, after exchanging heat with the bottom of the ethylene oxide absorber, is caused by a heat pump to liberate thermal energy and generate steam. Further, the liquid-phase part can be used as a heat source for the ethylene oxide refiner and/or the light ends stripper. Moreover, the gas from the top of the ethylene oxide stripper can be used as a heat source for the ethylene oxide refiner.

21 Claims, 7 Drawing Sheets

METHOD FOR RECOVERY OF ETHYLENE OXIDE

This is a continuation-in-part of copending application Ser. No. 878,113, filed June 25, 1986, which is now abandoned.

BACKGROUND OF THE INVENTION

1. Field of the Invention:

This invention relates to a method for the purification of ethylene oxide obtained by the catalytic gas-phase oxidation of ethylene with a molecular oxygen-containing gas. More particularly, to a process for the recovery of ethylene oxide by the steps of leading to an ethylene oxide absorber, an ethyl oxide-containing reaction product gas resulting from the catalytic gas-phase oxidation of ethylene with a molecular oxygen-containing gas in the presence of a silver catalyst thereby inducing absorption of the gas by an absorbent liquid and recovery of ethylene oxide, then forwarding the absorbent liquid now containing ethylene oxide of an ethylene oxide stripper. The bottom of the ethylene oxide stripper is then heated thereby inducing stripping of ethylene oxide from the top of the ethylene oxide stripper, and leading part of the liquid withdrawn through the bottom of the ethylene oxide stripper to the absorber to be recirculated therein as the absorbent liquid. This invention relates to a method for the recovery of ethylene oxide, which resides in lowering the heating energy of the ethylene oxide stripper, an ethylene oxide refiner and a light ends stripper.

2. Description of Prior Art:

In the step for the recovery of ethylene oxide, the ethylene oxide is obtained by allowing the gas produced by the reaction to be absorbed by an absorbent liquid having water as a main component thereby recovering ethylene oxide in the form of an aqueous solution and causing the aqueous solution to obtain ethylene oxide through stripping. Ethylene oxide is generally recovered as follows. The catalytic gas-phase oxidation of ethylene with a molecular oxygen-containing gas in the presence of a silver catalyst produces a reaction product gas containing ethylene oxide. This gas is introduced to an ethylene oxide absorber allowed therein to come into counterflow contact with an absorbent liquid having water as a main component thereof so as to effect recovery of an aqueous ethylene oxide solution. Then, this aqueous solution is forwarded to an ethylene oxide stripper and, by heating the bottom of the ethylene oxide stripper with steam, ethylene oxide is obtained from the solution. The aqueous solution which now contains substantially no ethylene oxide is withdrawn via the bottom of the stripper to be recirculated as the ethylene oxide absorbent liquid. The diffusate departing from the top of the ethylene oxide stripper and containing ethylene oxide, water, carbon dioxide, inert gases (nitrogen, argon, methane, ethane, etc.), low-boiling impurities such as formaldehyde, and high-boiling impurities such as acetaldehyde and acetic acid is purified by being passed through the step of dehydration, the step of separation of more volatile components, and the step for separation of heavyduty components, to give rise to ethylene oxide. (Refer, for example, to U.S. Pat. No. 3,165,539; 2,771,473; 4,028,070; 3,097,215; 3,217,466; 3,745,092; 3,729,899; 3,766,714; and 3,964,980.)

The method heretofore known to the art will be described specifically below.

With reference to FIG. 1, ethylene is subjected to catalytic gas-phase oxidation with a molecular oxygen-containing gas in the presence of a silver catalyst to produce a reaction product containing ethylene oxide. This gas is passed through a conduit 1 and fed to the lower part of an ethylene oxide absorber 2 in the form of a packed tower or a tray tower. An absorbent liquid is introduced via a conduit 3 into the upper part of the ethylene oxide absorber 2 and brought into counterflow contact in the tower with the reaction product gas to recover not less than 99% by weight of ethylene oxide present in the product gas. Such gases as that portion of ethylene oxide which has not been absorbed, oxygen, carbon dioxide, inert gases (nitrogen, argon, methane, and ethane), aldehydes, and acidic substances departing from the top of the ethylene oxide absorber 2 are forwarded via a conduit 4 and circulated to the carbon dioxide absorption step and/or the oxidation step. In this step of absorption, such lowboiling impurities as formaldehyde and such high-boiling impurities as acetaldehyde and acetic acid which are formed in the step of oxidation of ethylene other than ethylene, oxygen, carbon dioxide, and inert gases (nitrogen, argon, methane, and ethane), ethylene oxide, are immediately substantially completely absorbed. The bottom liquid of the ethylene oxide absorber 2 is passed through a conduit 5 to a heat exchanger 6, there to exchange heat with the bottom liquid of an ethylene oxide stripper and is thus heated to a temperature to 70° to 110° C. The hot bottom liquid of the ethylene oxide absorber 2 is then sent through a conduit 7 to a gas-liquid separation tank 8. The more volatile component of inert gas containing ethylene oxide and water is partly separated via a conduit 9. The absorbent liquid left behind after the more volatile gas has been expelled by flashing is passed through a conduit 10 and introduced to the upper part of an ethylene oxide stripper 11 kept under top pressure of 0.1 to 2 kg/cm$^2$G at a top temperature in the range of 85° to 120° C. and heated in a conduit 13 with a heating medium such as stem or a heat medium (produced by The Dow Chemical Company and marketed under trademark designation of "Dowtherm") circulated through a heater 12 annexed to the ethylene oxide stripper 11 or heated directly by feeding to the bottom of the ethylene oxide stripper 11. As the result, not less than 99% by weight of the ethylene oxide contained in the absorbent liquid is stripped. Part of the bottom liquid of the ethylene oxide stripper containing substantially no ethylene oxide and having a temperature of 100° to 150° C. is withdrawn via the bottom of the ethylene oxide stripper 11 and forwarded via conduits 14 and 15 to the heat exchanger 6, thereto exchange heat with the bottom liquid of the ethylene oxide absorber 2. The bottom liquid consequently deprived of heat is passed through a conduit 16 and further cooled by a cooler 17 having cooling water circulated through conduits 18 and 19 therein and passed to absorber 2 via conduits 20 and 3. Then, fresh water is introduced via a conduit 21 for the purpose of adjusting the ethylene glycol concentration in the absorbent liquid. An aqueous potassium hydroxide solution may be added into the absorbent liquid when necessary for the adjustment of the pH of the liquid. For the adjustment of the anti-foam agent concentration in the absorbent liquid, an anti-foam agent may be added into the ethylene oxide absorber 2. To prevent the by-produced ethylene glycol (arising from the hydrolysis of ethylene oxide and water), such low-boiling impurities as formaldehyde, and such high-boiling impurities as acetaldeyde and acetic acid from increasing in the absorbent liquid between the step of oxidation of ethylene with molecular oxygen and the step of stripping of ethylene oxide, the bottom liquid of the ethylene oxide stripper 11 is withdrawn via conduits 14 and 22 through the bottom of the ethylene oxide stripper 11 and forwarded to the step for concentration of the by-produced ethylene glycol.

In the meantime, the vapor containing ethylene oxide and obtained via the top of the ethylene oxide stripper 11 is forwarded via a conduit 23 to a condenser 24 having cooling water circulated through conduits 25 and 26 therein. The condensate consequently produced is returned via a conduit 27 to the top of the ethylene oxide stripper 11 and uncondensed vapor is introduced via a conduit 28 to a dehydrator 29.

The bottom liquid of dehydrator 29 is heated either by being sent through a conduit 31 which is kept heated by a heating medium such as steam or Dowtherm by a reboiler 30 annexed to the dehydrator 29 or directly by the introduction of steam into the lower part of the dehydrator 29. The water, containing substantially no ethylene oxide, is withdrawn via a conduit 32 from the bottom of the dehydrator 29.

From the top of the dehydrator 29, the vapor containing ethylene oxide is forwarded via a conduit 33 to a condenser 34 having cooling water or brine circulated through conduits 35 and 36 therein. The condensate consequently formed is returned via a conduit 37 to the top of the dehydrator 29. The uncondensed vapor in the condenser 34 is introduced via a conduit 39 to an ethylene oxide vent-scrubber (not shown). The remaining part of the condensate in the condenser 34 is introduced via a conduit 38 to a light ends stripper 40.

The supplied liquid is heated by being passed through a conduit 42 heated with a heating medium such as steam or Dowtherm by a heater 41 annexed to the light ends stripper 40. From the top of the light ends stripper 40, the ethylene oxide vapor containing other more volatile component is forwarded via a conduit 43 to a condenser 44 cooled by coolant circulated through conduits 45 and 46. The condensate consequently formed is returned via a conduit 47 to the top of the light ends stripper 40. The uncondensed vapor is introduced via a conduit 48 to an ethylene oxide vent-scrubber (not shown) for the recovery of ethylene oxide.

From the bottom of the light ends stripper 40, the bottom liquid is introduced via a conduit 49 to an ethylene oxide refiner 50.

Steam at a pressure of 0.5 to 3.0 kg/cm$^2$G is introduced via a conduit 59 to a heater 58 annexed to the ethylene oxide refiner 50. Rectification is then carried out with the bottom temperature of the ethylene oxide refiner 50 maintained at 35° to 85° C. and the bottom pressure of the tower maintained at 1.2 to 8.2 kg/cm$^2$G. The ethylene oxide vapor at a top temperature of 29° to 81° C. and top pressure of 1.0 to 8.0 kg/cm$^2$G is withdrawn via the top of the ethylene oxide refiner and forwarded via a conduit 51 to a condenser 52, there to be condensed. Part of the liquefied ethylene oxide is passed through a conduit 56 and introduced as a reflux liquid to the top of the ethylene oxide refiner 50. The remaining part of the liquefied ethylene oxide vapor is withdrawn via a conduit 57 as an ethylene oxide product.

The uncondensed vapor is condensed in the condenser 52 cooled by coolant passing through conduits 53 and 54 of the ethylene oxide refiner 50 and supplied via a conduit 55 to the ethylene oxide vent scrubber (not shown) for recovery of ethylene oxide.

The bottom liquid of the ethylene oxide refiner 50 is withdrawn via a conduit 67 when necessary for the separation of heavy-duty fractions of such high-boiling impurities as acetaldehyde, water, acetic acid etc.

Part of the bottom liquid from conduit 67 is circulated to reboiler 58 where it is heated by a heating medium injected into input 59.

The method of the purification of ethylene oxide described above, however, is not satisfactory in terms of the recovery of the heat of condensation of the vapor liberated through the top of the ethylene oxide stripper and the recovery of the thermal energy possessed by the liquid withdrawn through the bottom of the ethylene oxide stripper. Thus, this method has the disadvantage that a large volume of heat is wastefully discharged from the system. The conventional method has imposed the requirement of causing the bottom liquid of the ethylene oxide stripper which has a temperature of 100° to 150° C. to exchange heat with the bottom liquid of the ethylene oxide absorber thereby effecting recovery of heat and thereafter cooling the bottom liquid and reclaiming the cooled bottom liquid as the absorbent liquid for use in the ethylene oxide absorber. Further, the method for the purification of ethylene oxide has entailed the disadvantage that the heating carried out in the ethylene oxide stripper, the ethylene oxide refiner and the light ends stripper consumes a large volume of heating steam.

The object of the present invention, therefore, is to provide a novel method for the purification of ethylene oxide.

Another object of the present invention is to provide a method for the purification of ethylene oxide, which aims to promote effective utilization of the energy of the bottom liquid in the ethylene oxide stripper and aims to promote effective utilization of the thermal energy of the diffusate from the top of the ethylene oxide stripper.

SUMMARY OF THE INVENTION

The objects described above are accomplished by a method for the recovery of ethylene oxide, comprising the steps of introducing the gas resulting from catalytic gas-phase oxidation of ethylene with a molecular oxygen-containing gas and containing ethylene oxide to an ethylene oxide absorber and allowing the gas to come into counterflow contact therein into an absorbent liquid, circulating part of the gas departing from the top of the absorption tower to the step for oxidation of ethylene, introducing an ethylene oxide-containing bottom liquid of the absorber to an ethylene oxide stripper, causing the ethylene oxide stripper to liberate ethylene oxide through stripper via the top thereof, and forwarding the liquid withdrawn from the bottom of the ethylene oxide stripper to the ethylene oxide absorber, there to be used as the absorbent liquid circulately, which method is characterized by subjecting the liquid withdrawn from the bottom of the ethylene oxide stripper to a flashing treatment thereby separating the liquid into a vapor-phase part and a liquid-phase part, introducing the vapor-phase part in a compressed state to the bottom of the ethylene oxide stripper, and reclaiming the liquid-phase part as the absorbent liquid for use in the ethylene oxide absorber.

The aforementioned objects are further accomplished, in the aforementioned recovery of ethylene oxide, by a method for the purification of ethylene oxide, which comprises causing the liquid-phase part from the flashing step to exchange heat with the bottom liquid of the absorber through the medium of a heat exchanger, then recovering the thermal energy of absorbent liquid by means of a heat pump with ensuing emission of steam, further cooling the absorbent liquid which has already been cooled absorbent liquid for use as the absorbent liquid in the absorber.

The aforementioned objects are also accomplished, in the aforementioned recovery of ethylene oxide, by a method for the purification of ethylene oxide, which comprises reclaiming the liquid-phase part as a source of heat for use in a refiner. These objects are accomplished, in the aforementioned recovery of ethylene oxide, by a method for the purification of ethylene oxide, which comprises reclaiming the liquid-phase part of the flashing step as a source of heat for use in a light ends stripper. They are also accomplished in the aforementioned recovery of ethylene oxide by a method for the purification of ethylene oxide, which comprises reclaiming the liquid-phase part of the flashing step as a common source of heat for use in the ethylene oxide refiner and the light ends stripper. Further they are accomplished, in the aforementioned recovery of ethylene oxide, by a method for the purification of ethylene oxide, which comprises using the liquid-phase part as a source of heat in the ethylene oxide refiner and subsequently using the same liquid-phase part as a source of heat in the light ends stripper.

PREFERRED EMBODIMENT OF THE INVENTION

Figure 1:
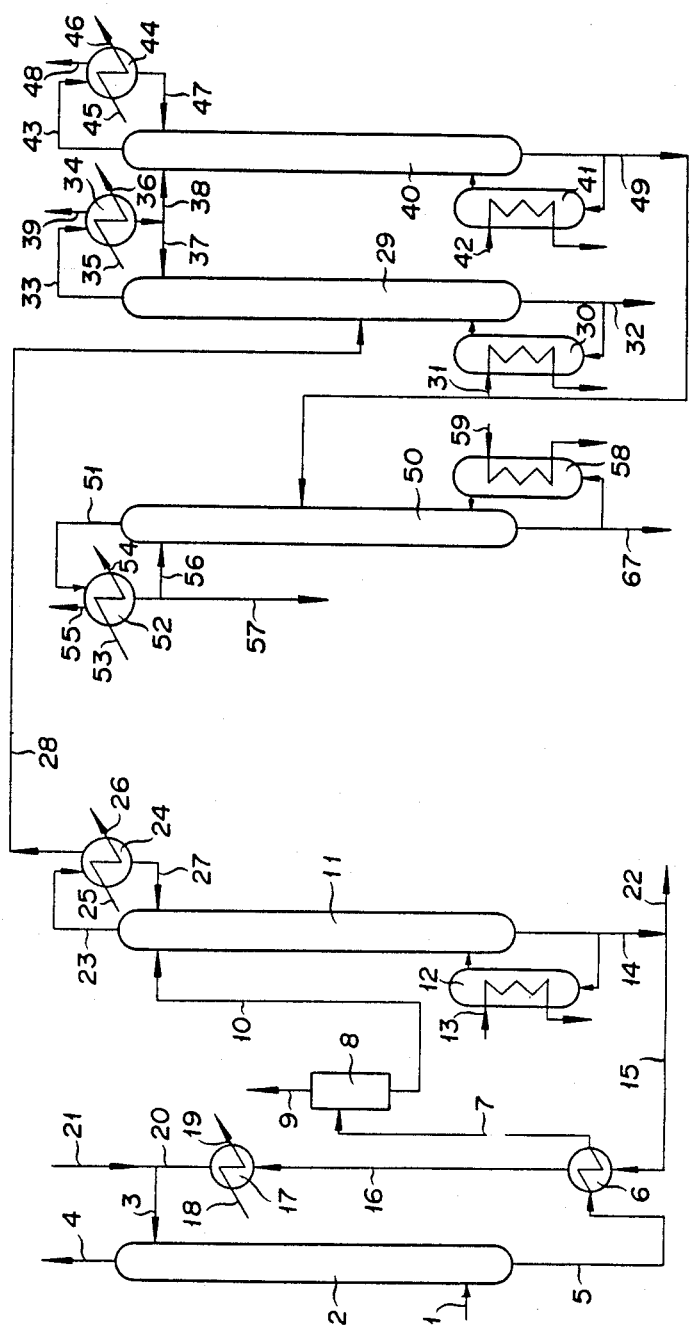
FIG. 1 is a flow chart illustrating a typical conventional method for the purification of ethylene oxide.

In the present invention, the temperature of the absorbent liquid which is supplied to the ethylene oxide absorber is in the range of 5° to 40° C., preferably 10° to 35° C. The absorbent liquid is controlled so that the pH of the liquid will maintain in the range of 5 to 12, preferably 6 to 11, the ethylene glycol concentration in the range of 1 to 40% by weight, preferably 5 to 30% by weight, the antifoam agent concentration at or above 0.1 ppm, preferably in the range of 1 to 100 ppm, and the water concentration in the range accounting for the balance. For the ethylene glycol concentration in the absorbent liquid to remain constant, part of the absorbent liquid being circulated through the ethylene oxide absorber and the ethylene oxide stripper is withdrawn through the bottom of the ethylene oxide stripper and forwarded to the by-produced ethylene glycol evaporator, there to be regulated when necessary by addition of fresh water. The adjustment of the pH is effected by the addition of a compound such as the hydroxide of an alkali metal like potassium or sodium or a carbonate thereof which is soluble in the absorbent liquid. Specifically, this additive is preferred to be potassium hydroxide or sodium hydroxide.

As the anti-foam agent for use in the present invention, any of the anti-foam agents can be used which are unreactive with ethylene oxide and the by-produced ethylene glycol, and are capable of defoaming the absorbent liquid. A water-soluble silicone emulsion which is a typical example of such anti-foam agents is used advantageously because it excels in dispersibility, stability of dilution, and thermal stability in the absorbent liquid.

As concerns the conditions for the operation of the ethylene oxide absorber, the ethylene oxide concentration in the reaction product gas is in the range of 0.5 to 5% by volume, preferably 1.0 to 4% by volume and the working pressure of the ethylene oxide absorber is in the range of 2 to 40 kg/cm$^2$G, preferably 10 to 30 kg/cm$^2$G. As concerns the operational condition of ethylene oxide stripper, the top pressure of the ethylene oxide stripper is in the range of 0.1 to 2 kg/cm$^2$G, preferably 0.3 to 0.6 kg/cm$^2$G to the top temperature of the ethylene oxide diffusion tower is in the range of 85° to 120° C., the bottom temperature of the ethylene oxide stripper is in the range of 100° to 150° C., and the bottom ethylene oxide concentration of the ethylene oxide stripper is not more than 30 ppm, preferably not more than 0.5 ppm.

Figure 2:
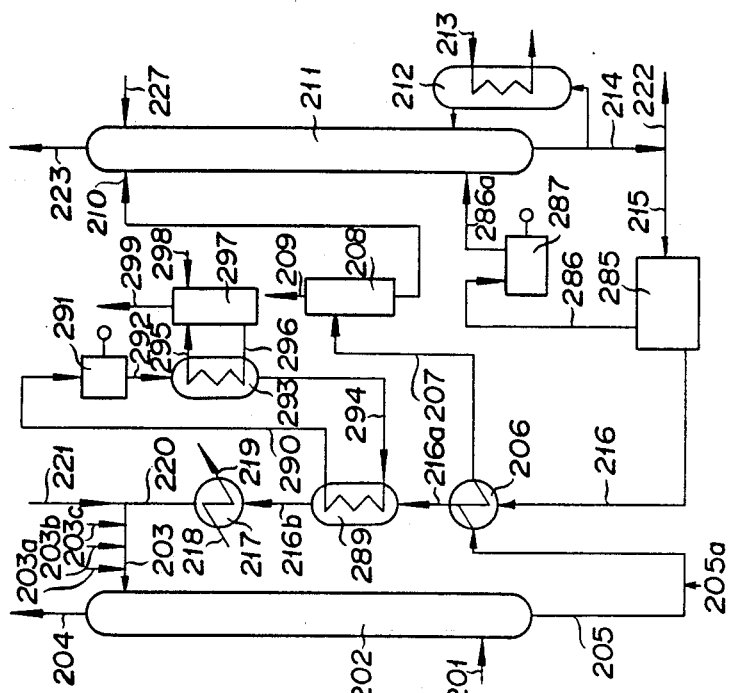

The first characteristic of the present invention illustrated in FIG. 2 resides in introducing the liquid emanating from the bottom of the ethylene oxide stripper into a flash tank operated under a pressure lower than that in the bottom of the ethylene oxide refiner and enabling it to generate lowpressure vapor. This generation of vapor is endothermic and, therefore, is effective in inducing a fall of temperature. The vapor thus generated has its pressure increased by an electrically driven centrifugal compressor, screw type compressor, or reciprocating compressor. The vapor under increased pressure is introduced to the vapor-phase part in the bottom of the ethylene oxide stripper, there to serve as part of the heat source for the ethylene oxide stripper and aid in economizing the consumption of steam as the heat source for the ethylene oxide stripper. The liquid left behind after the generation of the low-pressure vapor is caused to exchange heat with the liquid from the bottom of the ethylene oxide absorber, for further recovery of heat values.

In the meantime, the bottom liquid of the ethylene oxide absorber which was caused to exchange heat with the remaining bottom liquid of the ethylene oxide stripper is introduced to the top of the ethylene oxide stripper to obtain ethylene oxide. The major part of the diffusate emanating from the top of ethylene oxide stripper in this invention consists of ethylene oxide and water and the minor part thereof consists of carbon dioxide and minute amounts of oxygen, ethylene, inert gases (nitrogen, argon, methane, and ethane), low-boiling impurities like formaldehyde, and high-boiling impurities like acetaldehyde and acetic acid.

Figure 3:
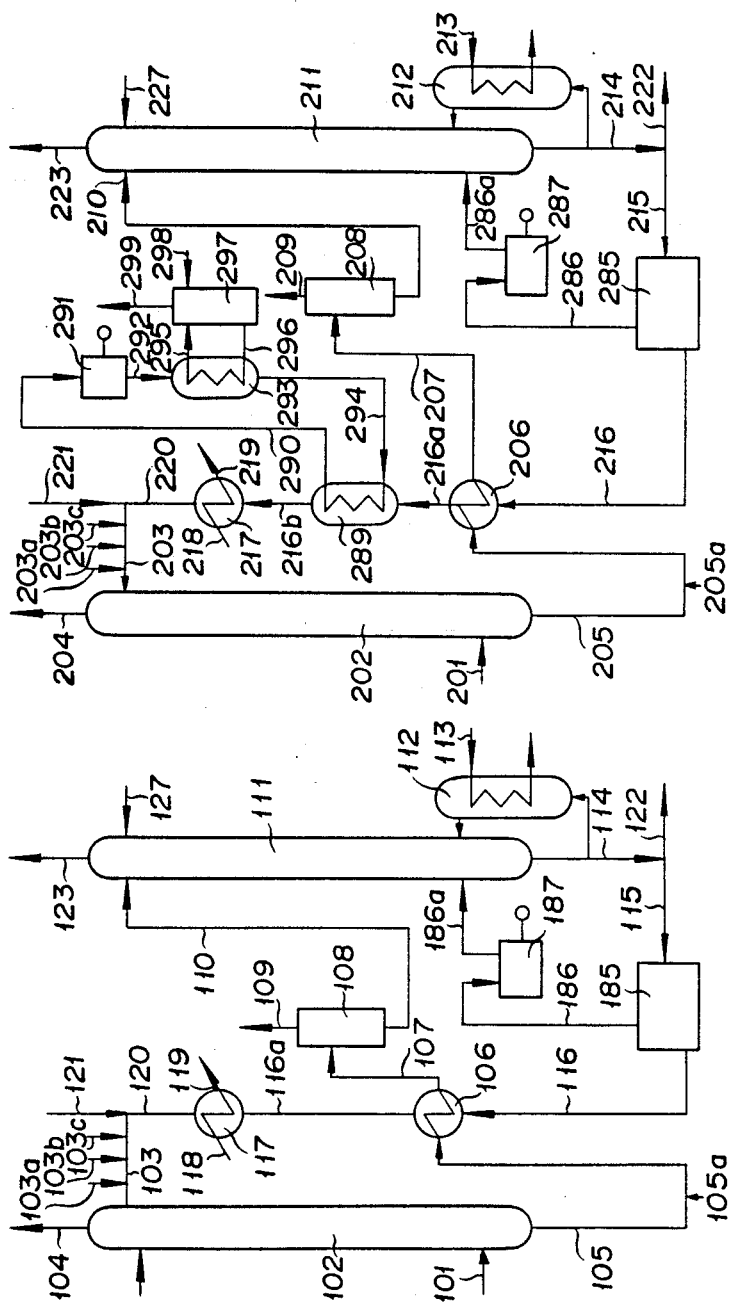
FIG. 2 is a flow chart illustrating a typical method for the purification of ethylene oxide in accordance with this invention and FIGS. 3–8 are flow charts illustrating other embodiments of the method of this invention for the purification of ethylene oxide.

The second characteristic of the prevent invention illustrated in FIG. 3 resides in recovering thermal energy possessed by the liquid withdrawn from the bottom of the ethylene oxide stripper and permitting effective use of the recovered thermal energy.

The bottom liquid of the ethylene oxide stripper which has emanated from the heat exchanger still retains available thermal energy. This thermal energy is recovered by a heat pump and utilized as a heat source for the step of ethylene oxide purification, particularly for the ethylene oxide refiner. This further recovery of thermal energy, therefore, promotes the economization of the steam consumed in the ethylene oxide refiner.

The refrigerant used as the operating fluid for the heat pump to be used in the present invention is alternately vaporized and condensed in the process of operation of the heat pump. In the selection of the refrigerant, therefore, due respect must be paid to the requirement that the refrigerant should be thermodynamically, thermally and chemically stable and, for the sake of handling, should be free from odor, toxicity, and explosiveness. As examples of the refrigerant usable in this invention, there may be cited fluorinated hydrocarbons such as R-11, R-12, R-22, R-113, and R-114, and hydrocarbons such as propane and pentane.

As concerns the operating conditions of the heat pump of this invention, the bottom liquid of the ethylene oxide stripper which has emanated from the bottom of the ethylene oxide stripper and exchanged heat with the bottom liquid of the ethylene oxide absorber by a heat exchanger and which consequently contains substantially no ethylene oxide enters the refrigerant evaporator at a temperature of 50° to 60° C. and vaporizes the refrigerant therein, with the result that the temperature of the bottom liquid of the ethylene oxide stripper is lowered by 5° to 20° C. The bottom liquid so cooled departs from the refrigerant evaporator and, as the cooled absorbent liquid for ethylene oxide, enters the ethylene oxide absorber.

The refrigerant which has been vaporized in the evaporator by the bottom liquid of the ethylene oxide stripper is compressed by a centrifugal, screw, or reciprocating type compressor to a pressure at which the saturation temperature of the refrigerant falls in the range of 80° to 100° C. By either of the two procedures indicated below, the refrigerant which has been given an increased pressure is caused to release its heat externally and is forwarded by a pump to the refrigerant evaporator to be re-used.

(1) The vapor of the refrigerant is directly forwarded to another refiner such as, for example, the reboiler of the ethylene oxide refiner (bottom temperature 35° to 85° C.) to be condensed, so that the heat of condensation is given to the bottom liquid of the refiner.

(2) The vapor of the refrigerant is forwarded to the refrigerant condenser, with the result that the latent heat of condensation is given to the fluid such as water in the refrigerant evaporator and the refrigerant is condensed.

The fluid such as, for example, water to which the refrigerant has given its heat is consequently heated to a temperature 5° to 10° C. lower than the temperature of the refrigerant and, by being flashed, enabled to generate low-pressure steam, which is recovered for use.

The third characteristic of the present invention resides in utilizing the heat content of the diffusate from the top of the ethylene oxide stripper. Since the diffusate from the top of the ethylene oxide stripper possesses thermal energy, it can be utilized as a heat source for the ethylene oxide refiner to economize the steam to be consumed as the heat source for the ethylene oxide refiner.

In the present invention, the temperature of the vapor introduced to the ethylene oxide dehydrator is maintained in the range of 5° to 60° C., preferably 10° to 50° C., and the ethylene oxide concentration in the vapor so supplied is in the range of 80 to 98% by weight.

As concerns the operation conditions of the ethylene oxide dehydrator, the top pressure of the dehydrator is in the range of 0 to 2 kg/cm$^2$G, preferably 0.3 to 0.6 kg/cm$^2$G, the top temperature of the dehydrator is in the range of 10° to 40° C., and the bottom temperature of the dehydrator is in the range of 100° to 130° C. The ethylene oxide concentration in the bottom of the dehydrator is not more than 100 ppm, preferably not more than 10 ppm.

In the present invention, the temperature of the liquid introduced to the light ends stripper is in the range of 0° to 50° C., preferably 5° to 30° C. The liquid so introduced has ethylene oxide as its major component and contains minute amounts of formaldehyde and other aldehydes besides water.

As concerns the operation conditions of the light ends stripper, the top pressure of the stripper is in the range of 1 to 10 kg/cm$^2$G, preferably 3 to 7 kg/cm$^2$G, the top temperature of the stripper is in the range of 30° to 90° C., and the bottom temperature of the stripper is in the range of 30° to 90° C.

The ethylene oxide concentration in the bottom of the light ends stripper is not less than 99.5% by weight, preferably not less than 99.95% by weight.

In the present invention, the ethylene oxide refiner is either a tray tower or a packed tower. In the case of the tray type distillation tower, examples of the type of tray include bubble cap tray, Uniflux tray, Turbogrid tray, lip tray, Flexy tray, sieve tray, and ballast tray. Examples of the packing for the packed type distillation tower are Raschig rings, Pall rings, saddle-shaped rings, spiral rings, MacMahon packing, Intalox metal packing, packing materials possessing pressure drop of not more than 10 mmHg per theoretical step, and superposed metal nets of woven or knit pattern.

In the present invention, the ethylene oxide refiner and light ends stripper are desired to be of a tray type possessing pressure drop of not more than 20 mmHg, preferably not more than 15 mmHg, per theoretical step or desired to be of a packed type possessing pressure drop of not more than 10 mmHg, preferably not more than 8 mmHg, per theoretical step.

The temperature of the liquid which is introduced to the ethylene oxide refiner in the present invention is in the range of 30° to 90° C., preferably 50° to 70° C. The liquid so introduced is controlled so that the ethylene oxide concentration will be not less than 99.5% by weight, preferably not less than 99.9% by weight.

As concerns the operation conditions of the ethylene oxide refiner, the top pressure of the refiner is in the range of 1.0 to 8.0 kg/cm$^2$G, preferably, 1.2 to 5.0 kg/cm$^2$G, the top temperature of the refiner is in the range of 29° to 81° C., the bottom temperature of the refiner is in the range of 35° to 85° C., and the ethylene oxide concentration in the bottom of the refiner is in the range of 30 to 90% by weight, preferably 40 to 80% by weight.

In this invention, the bottom liquid of the ethylene oxide refiner is a heavy-duty component consisting of such high-boiling impurities as acetaldehyde, water, acetic acid etc.

The fourth characteristic of the present invention, in the method of the aforementioned first characteristic, resides in causing the liquid-phase part which has undergone the flashing treatment to exchange heat with the ethylene oxide-containing bottom liquid of the ethylene oxide absorber, then using the resulting liquid as the heat source for the ethylene oxide refiner, subsequently utilizing the liquid as the heat source for the light ends stripper, cooling and leading the same liquid to the ethylene oxide absorber to be used therein again as the absorbent liquid.

The fifth characteristic of this invention, in the method of the aforementioned first characteristic, resides in causing the liquid-phase part which has undergone the flashing treatment to exchange heat with the ethylene oxide-containing bottom liquid of the ethylene oxide absorber, using the resulting liquid as the heat source for the light ends stripper, cooling the same liquid, and leading the cooled liquid to the ethylene oxide absorber, there to be used circulately therein as the absorbent liquid.

The sixth characteristic of the present invention, in the method of the first characteristic mentioned above, resides in causing the liquid-phase part which has undergone the flashing treatment to exchange heat with the ethylene oxide-containing bottom liquid of the ethylene oxide absorber, using the resulting liquid as the heat source for the refiner and as the heat source for the light ends stripper, then cooling the same liquid, and leading the cooled liquid to the ethylene oxide absorber to be used again therein as the absorbent liquid.

Now, the present invention will be described more specifically below with reference to the drawings.

Hereinbelow, for conciseness of description, not all item numbers illustrated in the various figures, are specifically described in that portion of the text relating to that particular figure. All items shown in the figures carrying the same "tens" and "unit" numbers, have the same function. Suffix letters or combination of suffix letters and numbers after said item numbers, signify branches of the same conduit. 100 items are in FIG. 1, 200 items in FIG. 3, 300 items in FIG. 4, 400 items in FIGS. 5 and 8, 500 items in FIG. 6 and 600 items in FIG. 7.

As illustrated in FIG. 2, the gas resulting from the catalytic gas-phase oxidation of ethylene with a molecular oxygen-containing gas in the presence of a silver catalyst is led via a conduit 101 to the lower part of a packed type or tray type ethylene oxide absorber 102. An absorbent liquid having a temperature of not more than 40° C. and a pH of not less than 6 and composed of 1 to 20% by weight of ethylene glycol, 1 to 50 ppm of an anti-foam agent (water-soluble silicone emulsion), and the balance of water is introduced via a conduit 103 into the absorption tower 102 and brought into counterflow contact with the gas, with the result that the ethylene oxide contained in the thus formed gas is absorbed by the absorbent liquid. Here, not less than 99% by weight of the ethylene oxide contained in the reaction product gas is recovered. Through the top of the absorption tower 102, such gases as ethylene, oxygen, carbon dioxide, inert gases (nitrogen, argon, methane, and ethane), aldehydes, and oxidative substances which have escaped being absorbed are circulated via a conduit 104 to the absorption step for carbon dioxide gas and/or the oxidation step.

At the absorption step for ethylene oxide, such low-boiling impurities as formaldehyde and such high-boiling impurities as acetaldehyde and acetic acid which have been formed in the oxidation step for ethylene besides ethylene, oxygen, carbon dioxide, inert gases (nitrogen, argon, methane, and ethane), and ethylene oxide are immediately, substantially, completely absorbed.

The bottom liquid of the absorber 102 is forwarded via a conduit 105 to a heat exchanger 106 and, through exchange of heat with the bottom liquid of the stripper, allowed to rise to temperature of 70° to 100° C., and then forwarded via a conduit 107 to a gas-liquid separation tank 108, with the result that the more volatile component gas of the inert gases entraining ethylene oxide and water is partly separated by a conduit 109. A liquid from an ethylene oxide vent-scrubber is introduced via a conduit 105a. The remaining absorbent liquid which has been stripped of the more volatile component gas by flashing is introduced via a conduit 110 to the upper part of the ethylene oxide stripper 111 kept under a pressure of 0.1 to 2 kg/cm$^2$G at a temperature of 90° to 120° C. and heated therein by introducing a heating medium such as steam or a heat medium (product of the Dow Chemical Company and marketed under trademark designation of "Dowtherm") through a conduit 113 inside a reboiler 112 of the ethylene oxide stripper 111 or by introducing steam directly to the bottom of the stripper. Part of the bottom liquid of the ethylene oxide stripper containing substantially no ethylene oxide and having a temperature of 100° to 150° C. is introduced via conduits 114 and 115 to a flash tank 185 operated under a pressure lower than that in the bottom of the ethylene oxide refiner (such as, for example, in the range of 0 to $-0.8$ kg/cm$^2$G, preferably 0 to $-0.5$ kg/cm$^2$G), to generate lowpressure vapor and induce a fall of the temperature of the liquid. The lowpressure vapor generated in the flash tank 185 is forwarded via a conduit 186 to a vapor compressor 187 and compressed therein to a pressure slightly higher than the bottom pressure of 0.5 to 2.4 kg/cm$^2$G (such as, for example, in the range of 0.6 to 2.5 kg/cm$^2$G) of the stripper 111. The compressed vapor is forwarded via a conduit 186a to the vapor-phase part in the bottom of the ethylene oxide stripper 111. The remaining liquid which has been flashed in the flash tank 185 is forwarded via a conduit 116 to a heat exchanger 106 and a cooler 117. Water may be introduced via a conduit 103a, an aqueous potassium hydroxide solution via a conduit 103b, and an anti-foam agent (water-soluble silicone emulsion) via a conduit 103c respectively into the ethylene oxide absorber 102 jointly through a conduit 103.

The remaining absorbent liquid withdrawn via a conduit 114 from the bottom of the stripper 111 is forwarded via a conduit 122 to a by-product ethylene glycol evaporator (not shown).

FIG. 3 illustrates another embodiment of the present invention. In a method similar to that illustrated in FIG. 2, the remaining liquid flashed in a flash tank 285 is introduced via a conduit 216 into a heat exchanger 206 and allowed to exchange heat with the bottom liquid of the ethylene oxide absorber. The bottom liquid of the ethylene oxide stripper which departs from the heat exchanger 206 flows through a refrigerant vaporizer 289 of a heat pump and then passes through a cooler 217. Water may be introduced via a conduit 203a, an aqueous potassium hydroxide solution via a conduit 203b, and an anti-foam agent (water-soluble silicone emulsion) via a conduit 203c into the ethylene oxide absorber 202 jointly through a conduit 203.

In the meantime, the remaining bottom liquid of ethylene oxide stripper which has been withdrawn via a conduit 214 from the bottom of the ethylene oxide stripper 211 can be forwarded via a conduit 222 to a by-produced ethylene glycol evaporator.

The refrigerant which has been vaporized in the refrigerant vaporizer 289 through heat exchange with the bottom liquid of the ethylene oxide stripper is forwarded via a conduit 290 to a refrigerant compressor 291 to be compressed therein and then forwarded via a conduit 292 to a refrigerant condenser 293, there to be condensed through transfer of its heat to an external fluid. The condensed refrigerant is forwarded via a conduit 294 again to the refrigerant vaporizer 289.

A conduit 299 is enabled to recover steam by circulating the water via a conduit 295 to a tank 297 and via a conduit 296 to the refrigerant condenser 293, and said water is supplied via a conduit 298 to a tank 297. The steam thus recovered can be effectively used as a heat source in the production step for ethylene oxide. Particularly this steam can be used in the ethylene oxide refiner. In FIG. 3, the reference numerals which are the sums of those of FIG. 2 each plus 100 denotes similar members.

Figure 4:
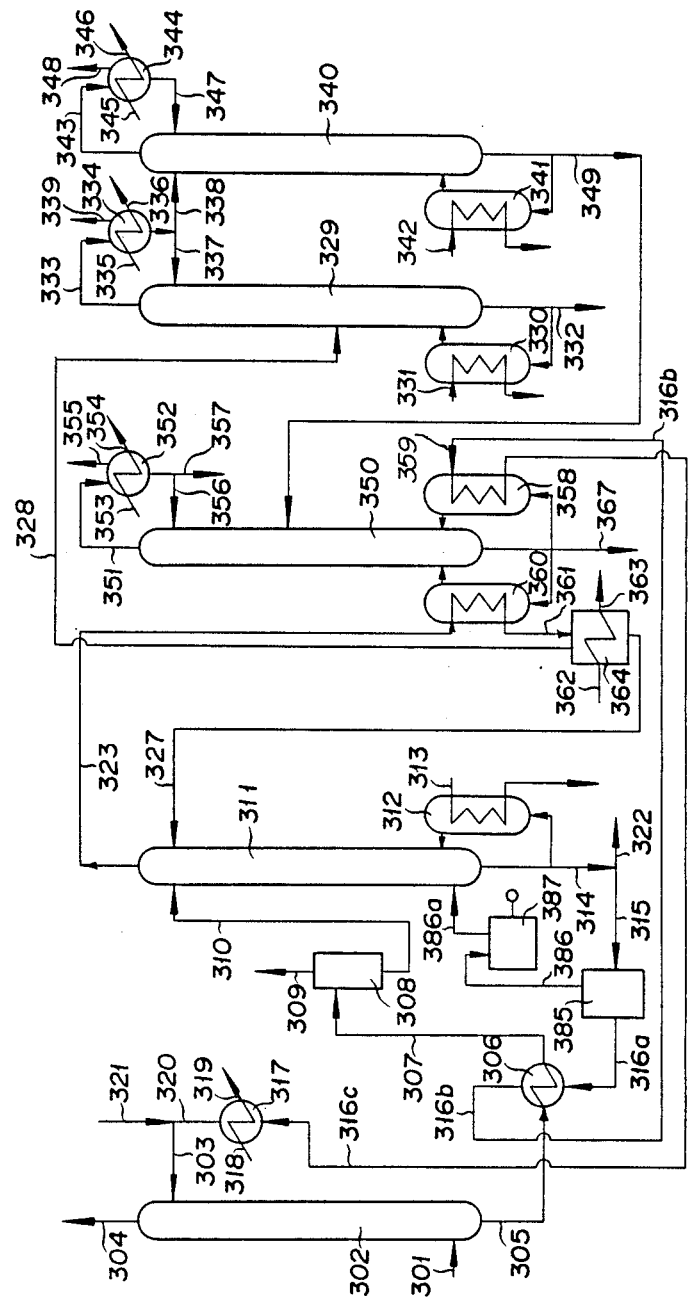

FIG. 4 illustrates another embodiment of the present invention. In a method similar to that illustrated in FIG. 2, from the bottom of an ethylene oxide stripper 311, part of the bottom liquid of the stripper which contains substantially no ethylene oxide and has a temperature of 100° to 150° C. is introduced via a conduit 314 and a conduit 315 to a flash tank 385, there to have the pressure thereof lowered to a pressure low enough to generate a low-pressure vapor and lower the temperature of the solution. The low-pressure vapor generated in the flash tank 385 is forwarded via a conduit 386 to a vapor compressor 387, there to be compressed to a pressure slightly higher than the bottom pressure, 0.5 to 2.4 kg/cm²G, of the ethylene oxide stripper 311. The compressed vapor is forwarded via a conduit 386a to the vapor-phase part in the bottom of the ethylene oxide stripper 311. The remaining liquid which has been flashed in the flash tank 385 is forwarded via a conduit 316a to a heat exchanger 306, caused to exchange heat therein with the ethylene oxide-containing bottom liquid of the ethylene oxide absorber. The resultant liquid is introduced via a conduit 316b into input 359 of a reboiler 358 of an ethylene oxide refiner 350 to be used as a heat source therein. Then, the liquid is forwarded via a conduit 316c to a cooler 317. Via a conduit 321, water, an aqueous potassium hydroxide solution, and an anti-foam agent (water-soluble silicone emulsion) may be added and, via a conduit 303, introduced into the ethylene oxide absorber 302.

In the meantime, for the purpose of preventing the by-produced ethylene glycol formed by the hydrolysis of the ethylene oxide present in the absorbent liquid with water, such low-boiling impurities as formaldehyde, and such high-boiling impurities as acetaldehyde and acetic acid from increasing during the oxidation step of ethylene with molecular oxygen and the stripping step of ethylene oxide, the remaining absorbent liquid withdrawn via a conduit 314 from the bottom of the ethylene oxide stripper 311 is forwarded via a conduit 322 to the by-produced ethylene glycol evaporator (not shown).

Separately, the ethylene oxide-containing vapor liberated through stripping from the top of the ethylene oxide stripper 311 is introduced via conduit 323 into a reboiler 360 of the ethylene oxide refiner 350 to be used as a heat source therein. Then, the resulting condensate and the uncondensed vapor is forwarded via a conduit 361 into a condenser 364 having cooling water circulated via a conduit 362 and a conduit 363 therein. The condensate is returned via a conduit 327 to the top of the ethylene oxide stripper 311 and the uncondensed vapor is introduced via a conduit 328 to a dehydrator 329.

This bottom liquid of the dehydrator 329 is heated either by heating a conduit 331 with a heating medium such as steam or Dowtherm (a product of the Dow Chemical Company) in the reboiler 330 of the dehydrator 329 or by directly introducing steam into the lower part of the dehydrator 329. From the bottom of the dehydrator 329, water containing substantially no ethylene oxide is withdrawn via a conduit 332.

From the top of the dehydrator 329, the vapor containing ethylene oxide is forwarded via a conduit 333 to a condenser 334 having cooling water or brine circulated through a conduit 335 and a conduit 336 therein. Part of the resulting condensate is returned via a conduit 337 to the top of the dehydrator 329. The uncondensed vapor in the condenser 334 is introduced via a conduit 339 to an ethylene oxide vent-scrubber (not shown). The other part of the condensate is introduced via a conduit 338 to a light ends stripper 340. From the top of the light ends stripper 340, the ethylene oxide vapor containing a more volatile component gas is forwarded via a conduit 343 to a condenser 344. The condensate is returned via a conduit 347 to the top of the light ends stripper 340. The uncondensed vapor is introduced via a conduit 348 to the ethylene oxide vent-scrubber (not shown) for recovery of ethylene oxide.

The bottom liquid of the light ends stripper 340 is introduced via a conduit 349 to a refiner 350.

The refiner 350 has two reboilers 360 and 358, so that the bottom liquid from the refiner 350 is introduced to both reboiler 360 and reboiler 358. One portion of the bottom liquid from the refiner 350 is heated in the reboiler 360 as stated previously, by the diffusate emanating from the top of the ethylene oxide stripper 311 and is returned to the refiner 350. The diffusate is then introduced into a heat exchanger 364 and the condensate thereof is returned to the stripper 311 via conduit 327. Another portion of the bottom liquid from the refiner 350 is heated in the reboiler 358 by the liquid from the flash drum 385 via conduit 316b and the liquid is returned to an absorber 302 via conduit 316c. Both heated bottom liquids in both reboilers respectively are returned to the refiner 350. Both reboilers are different in a temperature, because the reboiler 360 is heated by the diffusate (vapor) from the stripper 311, so the temperature is high, while the reboiler 358 is heated by the liquid from the flash drum 385 after heat-exchanging at a heat exchanger 306, so the temperature is lower than the reboiler 360. The rectification is carried out with the bottom temperature of the ethylene oxide refiner 350 controlled in the range of 35° to 85° C. and the bottom pressure of the ethylene oxide refiner in the range of 1.2 to 8.2 kg/cm²G. From the top of the ethylene oxide refiner, the ethylene oxide vapor having a top temperature of 29° to 81° C. and a top pressure of 1 to 8 kg/cm²G is forwarded via a conduit 351 to an ethylene oxide condenser 352, for condensation of ethylene oxide. Part of the condensed ethylene oxide is returned via a conduit 356 to the top of the ethylene oxide refiner 350 and the other part thereof is withdrawn as ethylene oxide product via a conduit 357.

The bottom liquid of the ethylene oxide refiner 350 is withdrawn via a conduit 367 when necessary for the separation of the heavy-duty portions of such high-boiling impurities as acetaldehyde and acetic acid. In FIG. 4, the reference numerals which are the sum of those in FIG. 2 each plus 200 denote similar members.

Figure 5:
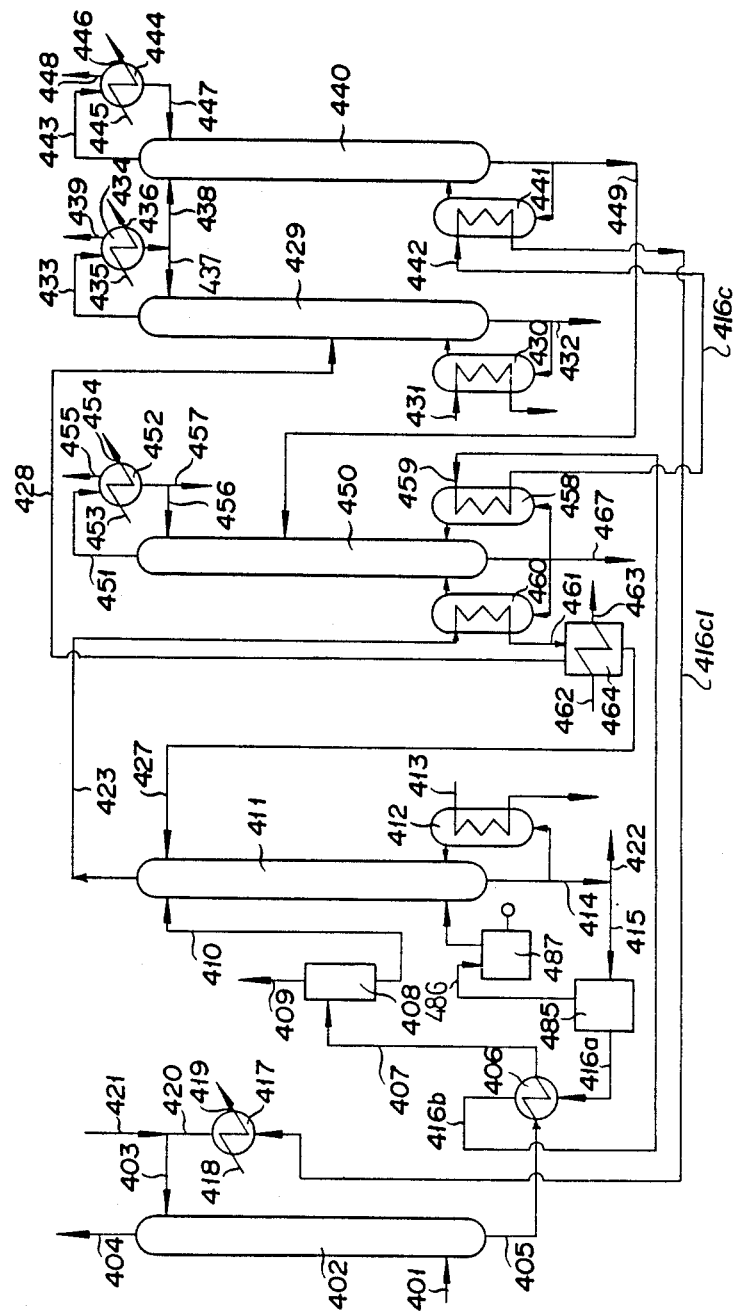

FIG. 5 illustrates yet another embodiment of the present invention. In a method similar to that of FIG. 4, the bottom liquid of the ethylene oxide stripper from a flash tank 485 which has been introduced to a reboiler 458 of a refiner and utilized as a heat source therein is introduced via a conduit 416C to input 442 of a reboiler 441 of a light ends stripper 440 and used as a heat source for the light ends stripper and then returned via a conduit 416C1 to a cooler 417. In all the other respects, the method of this embodiment is similar to that of FIG. 4. In FIG. 5, the reference numerals which are the sums of those of FIG. 4 each plus 100 denote similar members.

Figure 6:
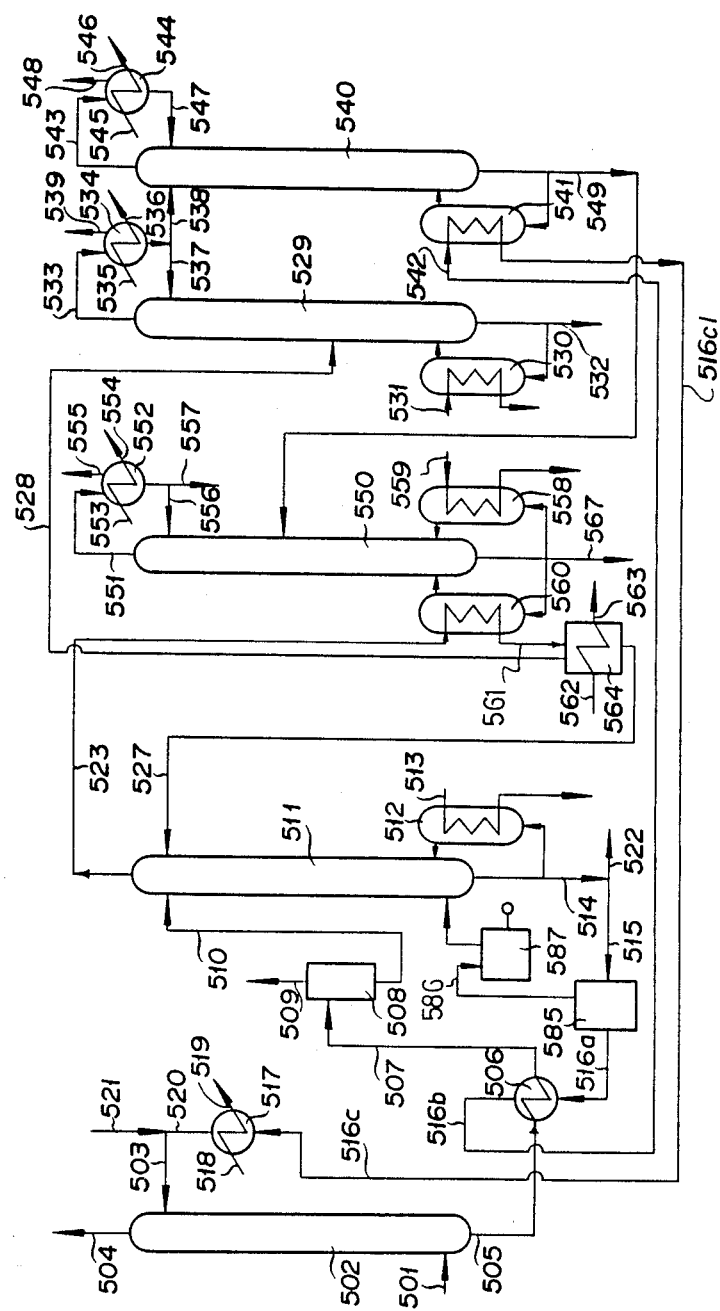

FIG. 6 illustrates still another embodiment of the present invention. In a method similar to that of FIG. 4, the liquid obtained by the flashing treatment in a flash tank 585 is forwarded to a heat exchanger 506 and then used as a heat source of a light ends stripper 540. For example, this liquid is introduced via a conduit 516b1 into input 542 of a reboiler 541 and utilized therein and then is forwarded via a conduit 516C1 to a cooler 517. In FIG. 6, the reference numerals which are the sums of those of FIG. 4 each plus 200 denote similar members.

Figure 7:
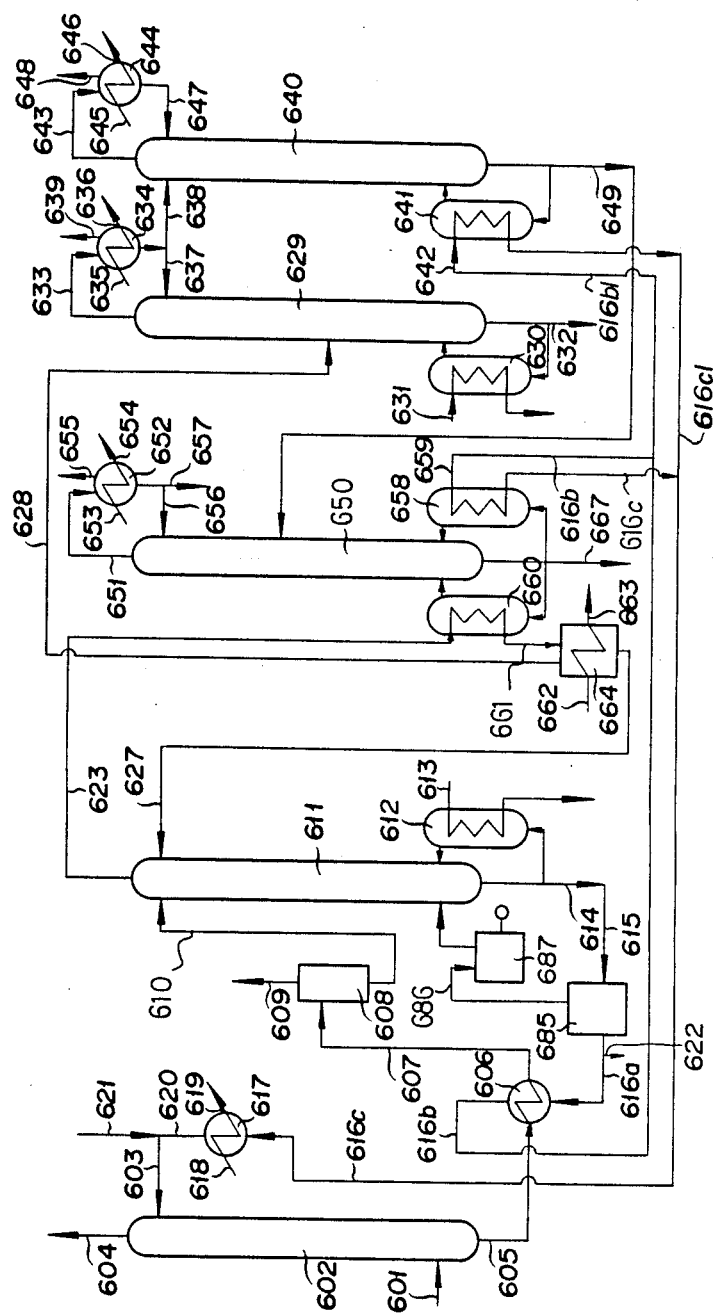

FIG. 7 illustrates a further embodiment of the present invention. In a method similar to that of FIG. 4, the liquid obtained by the flashing treatment in a flash tank 685 is passed through a heat exchanger 606 and then used as a joint heat source for an ethylene oxide refiner 650 and a light ends stripper 640. For example, this liquid is supplied via a conduit 616B to a reboiler 658 and via a branch 616B1 of conduit 616B to input 642 of a reboiler 641 and then forwarded via a conduit 616C1, to a cooler 617 branching into conduit 616C from reboiler 658. In FIG. 7, the reference numerals which are the sums of those in FIG. 4 each plus 300 denote similar members.

Figure 8:
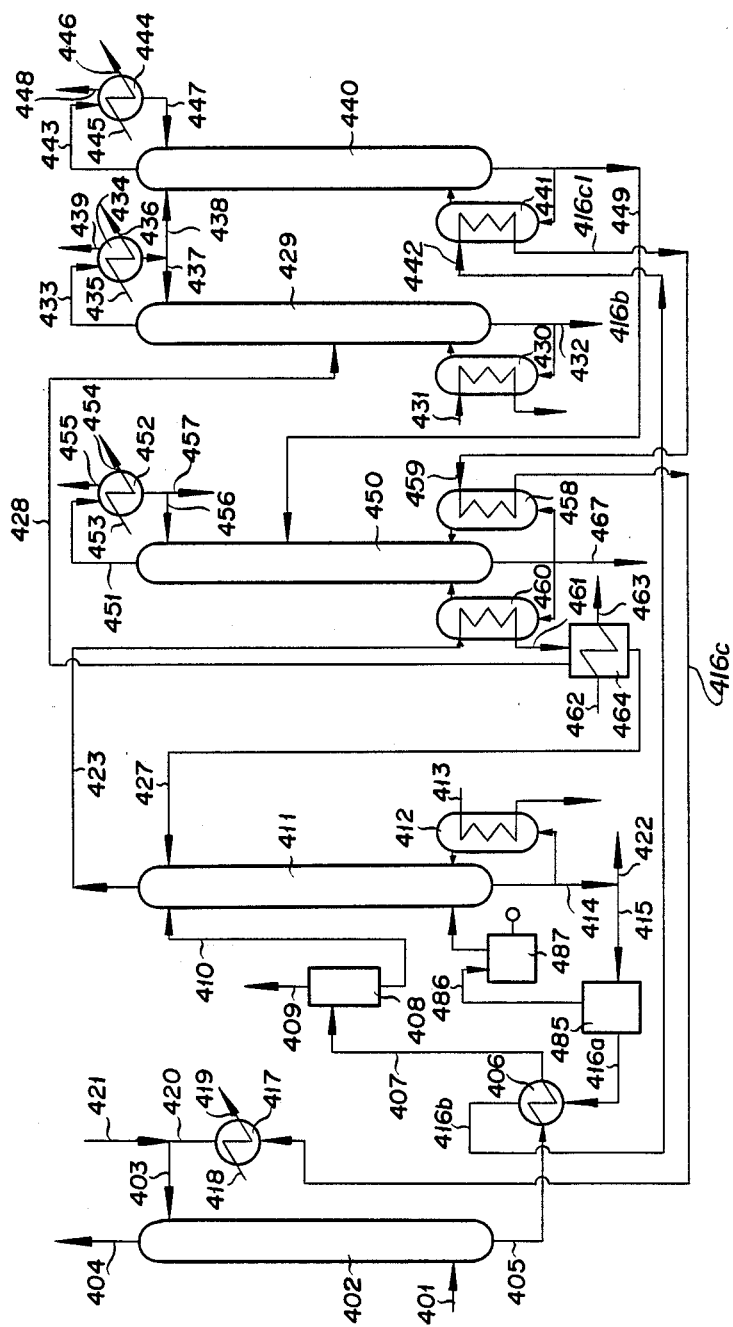

FIG. 8 illustrates a modification of the system of FIG. 5, wherein the output of flash tank 485 passes through conduit 416 via 416A and 416B to input 442 of reboiler 441 serving as a heat source for light end stripper 440. It then passes via conduit segment 416C1 to input 459 of reboiler 458, serving as a heat source for ethylene oxide refiner 450 and then via segment 416C to cooler 417.

Now, the present invention will be described more specifically below with reference to working examples. It should be noted, however, that the present invention is not limited solely to these working examples.

EXAMPLE 1

In an apparatus of FIG. 2, the gas resulting from the catalytic gas-phase oxidation of ethylene with a molecular oxygen-containing gas in the presence of a silver catalyst and consequently containing ethylene oxide was introduced via the conduit 101 to the lower part of the tray type ethylene oxide absorber 102. An absorbent liquid having a temperature of 29.6° C. and a pH of 6 and composed of 9.0% by weight of ethylene glycol, 3 ppm of an anti-foam agent (water-soluble silicone emulsion), and the balance of water was introduced via a conduit 103 into the upper part of the absorber 102 and brought into counterflow contact therein with the aforementioned gas, so as to allow the ethylene oxide present in the gas to be absorbed by the absorbent liquid. Here, not less than 99% by weight of the ethylene oxide present in the gas was recovered. From the top of the absorber 102, such gases as the ethylene, oxygen, carbon dioxide, inert gases (nitrogen, argon, methane, and ethane), aldehydes, and acidic substances which had escaped being absorbed were circulated via the conduit 104 to the absorption step for carbon dioxide gas and/or the oxidation step.

The bottom liquid of the ethylene oxide absorber 102 was forwarded via the conduit 105, a heat exchanger 106, and a conduit 107 to a gas-liquid separation tank 108 and the more volatile component gas containing ethylene oxide and water was separated by a conduit 109. The absorbent liquid remaining after separation of the more volatile component gas by flashing was introduced via a conduit 110 to the upper part of ethylene oxide stripper 111 and was heated therein by supplying steam via a conduit 113 to a reboiler 112 of the stripper 111. Consequently, from the bottom of the ethylene oxide stripper 111, the bottom liquid of the stripper containing substantially no ethylene oxide was withdrawn via a conduit 114. Part of the liquid was introduced via a conduit 115 to a flash tank 185, there to effect drop of pressure to atmospheric pressure, a fall of the temperature of the solution. The low-pressure vapor generated in the flash tank 185 was forwarded via a conduit 186 to a vapor compressor 187 and compressed therein to a pressure by 0.1 Kg/cm$^2$G higher than the bottom pressure, 0.5 Kg/cm$^2$G, of the stripper 111. The compressed vapor was forwarded via a conduit 186a into the vapor-phase part in the bottom of the stripper. The liquid remaining after the flashing treatment in the flash tank 185 was passed via a conduit 116 to the heat exchanger 106 and the cooler 117, admixed with water introduced via a conduit 103a an aqueous potassium hydroxide solution introduced via a conduit 103b, and an anti-foam agent (water-soluble silicone emulsion) introduced via a conduit 103C, and introduced via a conduit 103 into the absorber 102.

In the meantime, the remaining absorbent liquid withdrawn via a conduit 114 from the bottom of the ethylene oxide stripper 111 was forwarded via a conduit 122 to a by-produced ethylene glycol evaporator. Table 1 shows collectively the operating conditions of this process.

EXAMPLE 2

As illustrated in FIG. 3, in a method similar to that of Example 1, part of the liquid obtained by flashing in a flash tank 285 was introduced via a conduit 216 to a heat exchanger 206, caused to exchange heat therein with the bottom liquid of the ethylene oxide absorber and introduced via a conduit 216a to a refrigerant vaporizer 289. The refrigerant which had been vaporized in the refrigerant evaporator 289 by the bottom liquid of the ethylene oxide stripper was forwarded via a conduit 290 to a refrigerant compressor 291 to be compressed therein. The compressed refrigerant was forwarded via a conduit 292 to a refrigerant condenser 293 and condensed therein through transfer of heat to an external fluid. The condensed refrigerant was sent via a conduit 294 to the refrigerant vaporizer 289 again.

Steam was recovered in a conduit 299 by circulating the water via a conduit 296 to the refrigerant condenser 293 and a conduit 295 to a tank 297, and said water was supplied via a conduit 298 to the tank 297. The recovered steam was forwarded to a reboiler of an ethylene oxide refiner and used as a heat source therefor.

Table 2 shows collectively the conditions for continuous operation of this process.

EXAMPLE 3

As illustrated in FIG. 4, the gas formed by the catalytic gas-phase oxidation of ethylene with a molecular oxygen-containing gas in the presence of a silver catalyst and consequently containing ethylene oxide was introduced via a conduit 301 to the lower part of the tray type ethylene oxide absorber 302. An absorbent liquid having a temperature of 29.6° C. and a pH of 6 and composed of 9.0% by weight of ethylene glycol, 3 ppm of an anti-foam agent (water-soluble silicone emulsion), and the balance of water was introduced via a conduit 303 into the upper part of the ethylene oxide absorber 302 and brought into counterflow contact with the reaction product gas, with the result that the ethylene oxide present in the product gas was absorbed by the absorbent liquid. Here, not less than 99% by weight of the ethylene oxide present in the product gas was recovered. From the top of the ethylene oxide absorber 302, the ethylene oxygen, carbon dioxide, inert gases (nitrogen, argon, methane, and ethane), and impurities such as aldehydes and acidic substances which had escaped being absorbed, were circulated via a conduit 304 to the absorption step for carbon dioxide and/or the oxidation step.

In this absorption step, such low-boiling impurities as formaldehyde and such high-boiling impurities as acetaldehyde and acetic acid formed in the oxidation step for ethylene besides ethylene, oxygen, carbon dioxide, inert gases (nitrogen, argon, methane, and ethane), and ethylene oxide were substantially immediately completely absorbed.

The bottom liquid of the ethylene oxide absorber 302 was sent via a conduit 305 to a heat exchanger 306 and caused to exchange heat therein with the bottom liquid of the ethylene oxide stripper and allowed to reach an elevated temperature of 82.7° C. The hot liquid was forwarded via a conduit 307 to a gas-liquid separation tank 308. Consequently, a more volatile component gas containing ethylene oxide and water was separated. The absorbent liquid remaining after the separation of the more volatile component gas by flashing was introduced via a conduit 310 to the upper part of an ethylene oxide stripper 311 having a top pressure of 0.4 Kg/cm$^2$ G and a temperature of 87° C. Ethylene oxide was obtained from the top of the stripper by being heated with vapor supplied via a conduit 313 to a reboiler 312 of the ethylene oxide stripper 311.

In the meantime, the remaining absorbent liquid withdrawn via a conduit 314 from the bottom of the ethylene oxide stripper 311 was forwarded via a conduit 322 to a by-produced ethylene glycol evaporator.

From the bottom of the ethylene oxide stripper 311, the bottom liquid containing substantially no ethylene oxide was withdrawn via a conduit 314. Part of the withdrawn bottom liquid was supplied via a conduit 315 to a flash tank 385 to generate low-pressure vapor and induce a fall of the temperature of the solution through drop of pressure to −0.35 Kg/cm$^2$G. The low-pressure vapor generated in the flash tank 385 was sent via a conduit 386 to a vapor compressor 387 and compressed therein to a pressure by 0.6 Kg/cm$^2$G higher than the bottom pressure, 0.5 Kg/cm$^2$G, of the ethylene oxide stripper 311. The compressed vapor was introduced via a conduit 386a into the vapor-phase part in the bottom of the ethylene oxide stripper 311. The liquid remaining after the flashing treatment in the flash tank 385 was forwarded via a conduit 316a to the heat exchanger 306 and caused to exchange heat with the ethylene oxide-containing bottom liquid of the ethylene oxide absorber, forwarded via a conduit 316b to a reboiler 358 of an ethylene oxide refiner, then used as a heat source for the ethylene oxide refiner, forwarded via a conduit 316c to a cooler 317, admixed with water, an aqueous potassium hydroxide solution, and an anti-foam agent (water-soluble silicone emulsion) introduced via a conduit 321, and introduced via a conduit 303 into the ethylene oxide absorber 302.

The ethylene oxide-containing vapor obtained through diffusion from the top of the ethylene oxide stripper 311 was forwarded via a conduit 323 to a reboiler 360 of an ethylene oxide refiner 350 and used as a heat source therein. Then, the condensate and the uncondensed vapor was forwarded via a conduit 361 to a condenser 364 having cooling water circulated through a conduit 362 and a conduit 363 therein. The condensate was returned via a conduit 327 to the top of the ethylene oxide stripper 311 and the uncondensed vapor was introduced via a conduit 328 to a dehydrator 329.

The bottom liquid of dehydrator was heated with a reboiler 330 of the dehydrator 329 by passing steam through a conduit 331 into the reboiler 330. From the bottom of the dehydrator 329, the water containing substantially no ethylene oxide was withdrawn via a conduit 332.

From the top of the dehydrator 329, the ethylene oxide-containing vapor was forwarded via a conduit 333 to a condenser 334 having brine circulated through a conduit 335 and a conduit 336 therein. Part of the condensate was returned via a conduit 337 to the top of the dehydrator 329. The uncondensed vapor in the condenser 334 was introduced via a conduit 339 to an ethylene oxide vent-scrubber (not shown). The other part of the condensate was introduced via a conduit 338 to a light ends stripper 340 which is of a packed type packed with Pall rings possessing a pressure drop of not more than 5 mm Hg per theoretical step. From the top of the light ends stripper 340, the ethylene oxide vapor containing the more volatile component gas was forwarded via a conduit 343 to a condenser 344. The condensate was returned via a conduit 347 to the top of the light ends stripper 340 and the uncondensed vapor was introduced via a conduit 348 to the ethylene oxide vent-scrubber (not shown) for recovery of ethylene oxide. The bottom liquid of the light ends stripper 340 was introduced via a conduit 349 to an ethylene oxide refiner 350 which is of a packed type packed with Pall rings possessing a pressure drop of not more than 5 mm Hg per theoretical step. The heating of the bottom liquid of the ethylene oxide refiner 350 was carried out both by supplying the diffusate from the top of the ethylene oxide stripper 311 to a reboiler 360 of the ethylene oxide refiner 350 and by introducing the absorbent liquid for ethylene oxide from flash drum 385 via a conduit 316b to the reboiler 358 of the refiner 350. The liquid is returned to an absorber 302 via conduit 316c. Both heated bottom liquids in both reboilers respectively are returned to the refiner 350. The distillation was carried out with the bottom temperature of the ethylene oxide refiner 350 at 45° C. and the bottom pressure thereof at 2.0 Kg/cm$^2$ G. From the top of the ethylene oxide refiner, the ethylene oxide vapor having a top temperature of 39° C. and a top pressure of 1.8 Kg/cm$^2$ G was forwarded via a conduit 351 to the ethylene oxide condenser 352 to condense ethylene oxide. Part of the condensed ethylene oxide was introduced via a conduit 356 to the top of the ethylene oxide refiner 350 and the other part was withdrawn as ethylene oxide product via a conduit 357.

The uncondensed vapor in the ethylene oxide condenser 352 was introduced via a conduit 355 to the ethylene oxide vent-scrubber (not shown) for recovery of ethylene oxide.

The bottom liquid of the ethylene oxide refiner 350 was withdrawn via a conduit 367 for the separation of heavy-duty components such as high-boiling impurities like acetaldehyde and acetic acid.

Table 3 collectively shows the conditions for continuous operation of the process.

EXAMPLE 4

As illustrated in FIG. 5, in a method similar to that of Example 3, by using a light ends stripper and an ethylene oxide refiner which were of tray types equipped ballast trays possessing a pressure drop of not more than 10 mm Hg per theoretical step, the bottom liquid of an ethylene oxide stripper was caused by a heat exchanger 406 to exchange heat with the liquid from an ethylene oxide absorber 402, the resulting liquid was introduced via conduits 416b and 416c to a reboiler 458 of an ethylene oxide refiner 450 and used in heating the liquid inside the refiner 450, the liquid was then introduced via a conduit segment 416C through input 442 to a heater 441 of a light ends stripper 440 to heat the liquid in a light ends stripper 440, then, it was introduced via a conduit branch 416C1 and a cooler 417 and cooled thereby. The cooled liquid was circulated to the ethylene oxide absorber 402. In all the other respects, the method was similar to that of Example 3. Table 4 shows collectively the conditions for continuous operation of this process.

EXAMPLE 5

As illustrated in FIG. 6, in a method similar to that of Example 3, the bottom liquid of the ethylene oxide stripper was caused by a heat exchanger 506 to exchange heat with the liquid from an ethylene oxide absorber 502. The resulting liquid was introduced via a conduit 516b to a reboiler 541 of the light ends stripper 540 and used as a heat source therefor. The liquid was sent via a conduit 516c to a cooler 517 and cooled thereby. The cooled liquid was circulated via a conduit 520 and a conduit 503 to the ethylene oxide absorber 502. In all the other respects, the method was similar to that of Example 3.

Table 5 shows collectively the conditions for continuous operation of the process.

EXAMPLES 6-11

As illustrated in FIG. 7, in a method similar to that of Example 3, the bottom liquid of the ethylene oxide stripper was flashed in a flash tank 685 and then caused by a heat exchanger 606 to exchange heat with the liquid from the ethylene oxide absorber 602. The resulting liquid was parallely introduced via conduits 616B and 616B1 respectively to a reboiler 658 of an ethylene oxide refiner 650 and to a reboiler 641 of a light ends stripper 640 and used as a heat source therefor, then sent through conduits 616C and 616C1 via a conduit 616C to a cooler 617 and cooled therein, and circulated via conduits 620 and 603 to the ethylene oxide absorber 602. In all the other respects, the method was similar to that of Example 3. In the apparatus of FIG. 7, the same procedures as the above were carried out, except that operation conditions of component parts were changed.

Tables 6-11 show collectively the conditions for continuous operation of these processes.

Control

As illustrated in FIG. 1, in a method similar to that of Example 3, the bottom liquid of an ethylene oxide stripper 11 not yet treated by flashing was partly caused by a heat exchanger 6 to exchange heat with the liquid from the bottom of the ethylene oxide absorber 2, then cooled by a cooler 17, subsequently circulated to the ethylene oxide absorber and used as the absorbent liquid therefor. In all the other respects, the method was similar to that of Example 3.

Table 12 shows collectively the conditions for continuous operation of this process.

EXAMPLE 8

As illustrated in FIG. 8, in a method similar to that of Example 3, by using a light ends stripper and an ethylene oxide refiner which were of tray types equipped ballast trays possessing a pressure drop of not more than 10 mmHg per theoretical step, the bottom liquid of an ethylene oxide stripper was caused by a heat exchanger 406 to exchange heat with the liquid from an ethylene oxide absorber 402, the resulting liquid was introduced via conduits 416b to a reboiler 441 of light end stripper 440 and used in heating the liquid inside the refiner 450, the liquid was then introduced via a conduit 416C1 to a heater 458 of an ethylene oxide refiner 450 to heat the liquid in a light ends stripper 440, then, it was introduced via a conduit 416C to and a cooler 417 and cooled thereby. The cooled liquid was circulated to the ethylene oxide absorber 402. In all the other respects, the method was similar to that of Example 3. Table 13 shows collectively the conditions for continuous operation of this process.

TABLE 1

| Component part | Composition (% by weight) | | | | | | | | | | | | | |
|---|---|---|---|---|---|---|---|---|---|---|---|---|---|---|
| | 105 | 107 | 109 | 110 | 123 | 113 | 114 | 186 | 186a | 116 | 116a | 120 | 118 | 119 |
| Inert gas | 0.07 | 0.06 | 31.77 | | | | | | | | | | | |
| Carbon dioxide | 0.12 | 0.11 | 34.34 | 0.04 | 1.08 | | | | | | | | | |
| Ethylene oxide | 2.72 | 2.70 | 23.84 | 2.60 | 65.36 | | | | | | | | | |
| Water | 88.46 | 88.49 | 10.05 | 88.62 | 33.55 | | 91.19 | 99.79 | 99.79 | 91.00 | 91.00 | 91.00 | | |
| Ethylene glycol | 8.63 | 8.64 | | 8.74 | 0.01 | | 8.81 | 0.21 | 0.21 | 9.00 | 9.00 | 9.00 | | |
| Flow rate (kg/Hr) | 291200 | 308000 | 620 | 307380 | 12500 | | 308000 | 6800 | 6800 | 295600 | 295600 | 295600 | | |
| Pressure (kg/cm$^2$G) | | 3.4 | 3.4 | 3.4 | 0.4 | 2.2 | 0.5 | 0 | 0.6 | 0 | 5 | 5 | 3 | 3 |
| Temperature (°C.) | 49 | 93.5 | 93.3 | 93.3 | 93.1 | 135 | 113.8 | 101.5 | 140 | 101.5 | 55.8 | 29.6 | 25 | 40 |
| Steam (kg/Hr) | | | | | | 11300 | | | | | | | | |
| Cooling water (m$^3$/Hr) | | | | | | | | | | | | | 499 | 499 |

TABLE 2

| Component part | Composition (% by weight) | | | | | | | | | |
|---|---|---|---|---|---|---|---|---|---|---|
| | 205 | 207 | 209 | 210 | 223 | 213 | 214 | 286 | 286a | 216 |
| Inert gas | 0.07 | 0.06 | 31.77 | | | | | | | |
| Carbon dioxide | 0.12 | 0.11 | 34.34 | 0.04 | 1.08 | | | | | |
| Ethylene oxide | 2.72 | 2.70 | 23.84 | 2.60 | 65.36 | | | | | |
| Water | 88.46 | 88.49 | 10.05 | 88.62 | 33.55 | | 91.19 | 99.79 | 99.79 | 91.00 |
| Ethylene glycol | 8.63 | 8.64 | | 8.74 | 0.01 | | 8.81 | 0.21 | 0.21 | 9.00 |
| Flow rate (kg/Hr) | 291200 | 308000 | 620 | 307380 | 12500 | | 308000 | 6800 | 6800 | 295600 |
| Pressure (kg/cm$^2$G) | | 3.4 | 3.4 | 3.4 | 0.4 | 2.2 | 0.5 | 0 | 0.6 | 0 |
| Temperature (°C.) | 49 | 93.5 | 93.3 | 93.3 | 93.1 | 135 | 113.8 | 101.5 | 140 | 101.5 |
| Steam (kg/Hr) | | | | | | 11300 | | | | |
| Cooling water (m$^3$/Hr) | | | | | | | | | | |

| Component part | Composition (% by weight) | | | | | | |
|---|---|---|---|---|---|---|---|
| | 216a | 220 | 218 | 219 | 299 | 216b | 298 |
| Inert gas | | | | | | | |
| Carbon dioxide | | | | | | | |
| Ethylene oxide | | | | | | | |
| Water | 91.00 | 91.00 | | | | 91.00 | 100 |
| Ethylene glycol | 9.00 | 9.00 | | | | 9.00 | 0 |
| Flow rate (kg/Hr) | 295600 | 295600 | | | | 295600 | 3600 |
| Pressure (kg/cm$^2$G) | 5 | 5 | 3 | 3 | −0.61 | 5 | |
| Temperature (°C.) | 55.8 | 29.6 | 25 | 40 | 75 | 49 | 75 |
| Steam (kg/Hr) | | | | | 3600 | | |
| Cooling water (m$^3$/Hr) | | | 370 | 370 | | | |

TABLE 3

| Component part | Composition (% by weight) | | | | | | | | | |
|---|---|---|---|---|---|---|---|---|---|---|
| | 307 | 309 | 310 | 313 | 314 | 318 | 319 | 323 | 362 | 363 |
| Inert gas | 0.07 | 39.72 | | | | | | | | |
| Carbon dioxide | 0.11 | 36.52 | 0.01 | | | | | 1.49 | | |
| Ethylene oxide | 2.66 | 17.21 | 2.64 | | | | | 73.21 | | |
| Water | 91.62 | 6.55 | 91.80 | | 94.51 | | | 25.30 | | |
| Ethylene glycol | 5.54 | | 5.55 | | 5.49 | | | | | |
| Others | | | | | | | | | | |
| Flow rate (kg/Hr) | 310900 | 510 | 310390 | | 315100 | | | 11700 | | |
| Pressure (kg/cm$^2$G) | 3.4 | 3.4 | 3.4 | 2.2 | 0.4 | 3 | 3 | 0.4 | 3 | 3 |
| Temperature (°C.) | 82.7 | 82.6 | 82.6 | 135 | 110 | 25 | 40 | 87.0 | 25 | 35 |
| Steam (kg/Hr) | | | | 7500 | | | | | | |
| Cooling water (m$^3$/Hr) | | | | | | 270 | 270 | | 14 | 14 |

| Component part | Composition (% by weight) | | | | | |
|---|---|---|---|---|---|---|
| | 328 | 356 | 357 | 386 | 316a | 316b |
| Inert gas | | | | | | |
| Carbon dioxide | 2.02 | | | | | |
| Ethylene oxide | 94.19 | ≈100 | ≈100 | | | |
| Water | 3.79 | | | 99.91 | 94.28 | 94.28 |
| Ethylene glycol | | | | 0.09 | 5.72 | 5.72 |
| Others | | | | | | |
| Flow rate (kg/Hr) | 8600 | 23700 | 7640 | 12800 | 298300 | 298300 |
| Pressure (kg/cm$^2$G) | 0.3 | 1.8 | 1.8 | −0.35 | 3 | 3 |
| Temperature (°C.) | 50 | 35 | 35 | 87.5 | 87.5 | 56.5 |
| Steam (kg/Hr) | | | | | | |
| Cooling water (m$^3$/Hr) | | | | | | |

TABLE 4

| Component part | Composition (% by weight) | | | | | | | | | | | | | | |
|---|---|---|---|---|---|---|---|---|---|---|---|---|---|---|---|
| | 407 | 409 | 410 | 413 | 423 | 462 | 463 | 428 | 449 | 456 | 457 | 486 | 416b | 442 | 416c |
| Inert gas | 0.07 | 39.72 | | | | | | | | | | | | | |
| Carbon dioxide | 0.11 | 36.52 | 0.06 | | 1.49 | | | 2.02 | | | | | | | |
| Ethylene oxide | 2.66 | 17.21 | 2.64 | | 73.21 | | | 94.19 | 99.97 | ≈100 | ≈100 | | | | |
| Water | 91.62 | 6.55 | 91.75 | | 25.30 | | | 3.79 | 0.01 | | | 99.91 | 94.28 | 94.28 | 94.28 |
| Ethylene glycol | 5.54 | | 5.55 | | | | | | | | | 0.09 | 5.72 | 5.72 | 5.72 |
| Others | | | | | | | | | 0.02 | | | | | | |
| Flow rate (kg/Hr) | 310900 | 510 | 310390 | | 11700 | | | 8600 | 7700 | 23700 | 7640 | 12800 | 298300 | 298300 | 298100 |
| Pressure (kg/cm$^2$G) | 3.4 | 3.4 | 3.4 | 2.2 | 0.4 | 3.0 | 3.0 | 0.3 | 2.0 | 1.8 | 1.8 | −0.35 | 3 | 3 | 3 |
| Temperature (°C.) | 82.7 | 82.6 | 82.6 | 135 | 87.0 | 25 | 35 | 50 | 42 | 35 | 35 | 87.5 | 56.5 | 48.3 | 45.5 |
| Steam (kg/Hr) | | | | 7500 | | | | | | | 4700 | | | | |

TABLE 4-continued

| Component part | Composition (% by weight) | | | | | | | | | | | | | | |
|---|---|---|---|---|---|---|---|---|---|---|---|---|---|---|---|
| | 407 | 409 | 410 | 413 | 423 | 462 | 463 | 428 | 449 | 456 | 457 | 486 | 416b | 442 | 416c |
| Cooling water (m³/Hr) | | | | | | 14 | 14 | | | | | | | 499 | |

TABLE 5

| Component part | Composition (% by weight) | | | | | | | | | | | | | | |
|---|---|---|---|---|---|---|---|---|---|---|---|---|---|---|---|
| | 507 | 509 | 510 | 513 | 523 | 562 | 563 | 528 | 549 | 559 | 556 | 557 | 586 | 516B | 516c |
| Inert gas | 0.07 | 39.72 | | | | | | | | | | | | | |
| Carbon dioxide | 0.11 | 36.52 | 0.06 | | 1.49 | | | 2.02 | | | | | | | |
| Ethylene oxide | 2.66 | 17.21 | 2.64 | | 73.21 | | | 94.19 | 99.97 | | ≃100 | ≃100 | | | |
| Water | 91.62 | 6.55 | 91.75 | | 25.30 | | | 3.79 | 0.01 | | | | 99.91 | 94.28 | 94.28 |
| Ethylene glycol | 5.54 | | 5.55 | | | | | | | | | | 0.09 | 5.72 | 5.72 |
| Others | | | | | | | | | 0.02 | | | | | | |
| Flow rate (kg/Hr) | 310900 | 510 | 310390 | | 11700 | | | 8600 | 7700 | | 23700 | 7640 | 12800 | 298300 | 298300 |
| Pressure (kg/cm²G) | 3.4 | 3.4 | 3.4 | 2.2 | 0.4 | 3.0 | 3.0 | 0.3 | 2.0 | 2.2 | 1.8 | 1.8 | −0.35 | 3 | 3 |
| Temperature (°C.) | 82.7 | 82.6 | 82.6 | 135 | 87.0 | 25 | 35 | 50 | 42 | 135 | 35 | 35 | 87.5 | 56.5 | 53.7 |
| Steam (kg/Hr) | | | | 7500 | | | | | | 4700 | | | | | |
| Cooling water (m³/Hr) | | | | | | 14 | 14 | | | | | | | | |

TABLE 6

| Component part | Unit (Kg mol/Hr) | | | | | | | | | |
|---|---|---|---|---|---|---|---|---|---|---|
| | 605 | 609 | 613 | 616a | 616b | 616c | 623 | 627 | 628 | 632 |
| Inert gas | 4.97 | 4.63 | | | | | 0.34 | | 0.34 | |
| Carbon dioxide | 9.41 | 5.32 | | | | | 4.09 | | 4.09 | |
| Ethylene oxide | 283.74 | 4.79 | | 0.16 | 0.15 | 0.15 | 279.93 | 7.14 | 272.79 | |
| Water | 19164.0 | 3.83 | | 19628.0 | 18666.79 | 18666.79 | 217.47 | 169.79 | 47.68 | 47.67 |
| Ethylene glycol | 116.52 | | | 122.52 | 116.52 | 116.52 | 0.01 | 0.01 | | |
| Others | | | | | | | | | | |
| Flow rate (kg-mol/Hr) | 19598.64 | 18.57 | | 19750.68 | 18783.46 | 18783.46 | 501.84 | 176.94 | 324.90 | 47.67 |
| Pressure (kg/cm²abs) | 6.0 | 3.0 | 3.2 | 0.8824 | 5 | 5 | 1.4 | 6 | 1.35 | 1.4 |
| Temperature (°C.) | 52.5 | 96.2 | 135 | 95.8 | 61.4 | 43.2 | 96.1 | 60.0 | 60 | 108.8 |
| Steam (kg/Hr) | | | 12218 | | | | | | | |
| Cooling water (m³/Hr) | | | | | | | | | | |

| Component part | Unit (Kg mol/Hr) | | | | | | |
|---|---|---|---|---|---|---|---|
| | 638 | 639 | 648 | 649 | 657 | 667 | 686 |
| Inert gas | | 0.34 | | | | | |
| Carbon dioxide | 1.54 | 2.55 | 1.54 | | | | |
| Ethylene oxide | 265.17 | 7.62 | 4.03 | 261.14 | 256.15 | 4.99 | |
| Water | 0.01 | | | 0.01 | | 0.01 | 633.19 |
| Ethylene glycol | | | | | | | |
| Others | | | | | | | |
| Flow rate (kg-mol/Hr) | 266.72 | 10.51 | 5.57 | 261.15 | 256.15 | 5.00 | 633.19 |
| Pressure (kg/cm²abs) | 4.0 | 1.3 | 1.3 | 1.4 | 2.5 | 2.9 | 0.882 |
| Temperature (°C.) | 8.0 | 8.0 | 8.0 | 18.3 | 35 | 39.7 | 95.8 |
| Steam (kg/Hr) | | | | | | | |
| Cooling water (m³/Hr) | | | | | | | |

Pressure of the top of the ethylene oxide stripping tower: 1.4 kg/cm² ᵃ Amount of the bottom liquid of the ethylene oxide stripping tower to be flashed: 11410 kg/Hr

TABLE 7

| Component part | Unit (Kg mol/Hr) | | | | | | | | | |
|---|---|---|---|---|---|---|---|---|---|---|
| | 605 | 609 | 613 | 616a | 616b | 616c | 623 | 627 | 628 | 632 |
| Inert gas | 4.97 | 4.85 | | | | | 0.12 | | 0.12 | |
| Carbon dioxide | 9.41 | 7.50 | | | | | 1.91 | | 1.91 | |
| Ethylene oxide | 283.74 | 17.64 | | 0.15 | 0.14 | 0.14 | 282.73 | 28.78 | 253.95 | |
| Water | 19164.0 | 20.68 | | 19969.0 | 18104.48 | 18104.48 | 238.51 | 221.03 | 17.48 | 17.46 |
| Ethylene glycol | 116.52 | | | 128.52 | 116.52 | 116.52 | 0.03 | 0.03 | | |
| Others | | | | | | | | | | |
| Flow rate (kg-mol/Hr) | 19578.64 | 50.67 | | 20097.67 | 18221.14 | 18221.14 | 523.3 | 249.84 | 273.46 | 17.46 |
| Pressure (kg/cm²abs) | 6.0 | 3.0 | 3.2 | 1.824 | 5 | 5 | 3.0 | 6 | 2.75 | 3 |
| Temperature (°C.) | 52.5 | 105.1 | 135 | 117 | 60.6 | 46.6 | 108.5 | 60.1 | 60 | 133 |
| Steam (kg/Hr) | | | 14793 | | | | | | | |
| Cooling water | | | | | | | | | | |

TABLE 7-continued

| | Unit (Kg mol/Hr) | | | | | | |
|---|---|---|---|---|---|---|---|
| ($m^3$/Hr) | | | | | | | |

| | Unit (Kg mol/Hr) | | | | | | |
|---|---|---|---|---|---|---|---|
| Component part | 638 | 639 | 648 | 649 | 657 | 667 | 686 |
| Inert gas | | 0.12 | | | | | |
| Carbon dioxide | 1.22 | 0.69 | 1.22 | | | | |
| Ethylene oxide | 249.78 | 4.17 | 3.09 | 246.69 | 241.71 | 4.98 | |
| Water | 0.02 | | | 0.02 | | 0.02 | 767.37 |
| Ethylene glycol | | | | | | | |
| Others | | | | | | | |
| Flow rate (kg-mol/Hr) | 251.02 | 4.98 | 4.31 | 246.71 | 241.71 | 5.00 | 767.37 |
| Pressure (kg/$cm^2$abs) | 4 | 2.3 | 3.5 | 3.6 | 2.5 | 2.9 | 1.824 |
| Temperature (°C.) | 34.1 | 34 | 35 | 46.7 | 35 | 39.7 | 117 |
| Steam (kg/Hr) | | | | | | | |
| Cooling water ($m^3$/Hr) | | | | | | | |

Pressure of the top of the ethylene oxide stripping tower: 3.0 kg/$cm^2$ a Amount of the bottom liquid of the ethylene oxide stripping tower to be flashed: 13828 kg/Hr

TABLE 8

| | Unit (Kg mol/Hr) | | | | | | | | | |
|---|---|---|---|---|---|---|---|---|---|---|
| Component part | 605 | 609 | 613 | 616a | 616b | 616c | 623 | 627 | 628 | 632 |
| Inert gas | 4.97 | 4.46 | | | | | 0.51 | | 0.51 | |
| Carbon dioxide | 9.41 | 4.1 | | | | | 5.31 | | 5.31 | |
| Ethylene oxide | 283.74 | 2.36 | | 0.16 | 0.15 | 0.15 | 278.15 | 2.93 | 275.22 | |
| Water | 19164.0 | 1.45 | | 19628.0 | 18666.79 | 18666.79 | 118.5 | 70.14 | 48.36 | 48.34 |
| Ethylene glycol | 116.52 | | | 122.52 | 116.52 | 116.52 | | | | |
| Others | | | | | | | | | | |
| Flow rate (kg-mol/Hr) | 19578.64 | 12.37 | | 19750.68 | 18783.46 | 18783.46 | 402.47 | 73.07 | 329.40 | 48.34 |
| Pressure (kg/$cm^2$abs) | 6 | 3.0 | 3.2 | 0.519 | 5 | 5 | 1.4 | 6 | 1.35 | 1.4 |
| Temperature (°C.) | 52.5 | 72.3 | 135 | 81.9 | 60.7 | 39.3 | 76.6 | 60.1 | 60 | 108.8 |
| Steam (kg/Hr) | | | 8438 | | | | | | | |
| Cooling water ($m^3$/Hr) | | | | | | | | | | |

| | Unit (Kg mol/Hr) | | | | | | |
|---|---|---|---|---|---|---|---|
| Component part | 638 | 639 | 648 | 649 | 657 | 667 | 686 |
| Inert gas | | 0.51 | | | | | |
| Carbon dioxide | 1.52 | | 1.52 | | | | |
| Ethylene oxide | 263.88 | 11.34 | 3.85 | 260.03 | 255.05 | 4.98 | |
| Water | 0.02 | | | 0.02 | | 0.02 | 1205.55 |
| Ethylene glycol | | | | | | | |
| Others | | | | | | | |
| Flow rate (kg-mol/Hr) | 265.42 | 15.64 | 5.37 | 260.05 | 255.05 | 5.00 | 1205.55 |
| Pressure (kg/$cm^2$abs) | 1.4 | 1.3 | 1.3 | 1.4 | 2.5 | 2.9 | 0.519 |
| Temperature (°C.) | 8 | 8 | 8 | 18 | 35 | 39.7 | 81.9 |
| Steam (kg/Hr) | | | | | | | |
| Cooling water ($m^3$/Hr) | | | | | | | |

Pressure of the top of the ethylene oxide stripping tower: 1.4 kg/$cm^2$ a Amount of the bottom liquid of the ethylene oxide stripping tower to be flashed: 21724 kg/Hr

TABLE 9

| | Unit (Kg mol/Hr) | | | | | | | | | |
|---|---|---|---|---|---|---|---|---|---|---|
| Component part | 605 | 609 | 613 | 616a | 616b | 616c | 623 | 627 | 628 | 632 |
| Inert gas | 4.97 | 4.69 | | | | | 0.28 | | 0.28 | |
| Carbon dioxide | 9.41 | 5.84 | | | | | 3.57 | | 3.57 | |
| Ethylene oxide | 283.74 | 6.30 | | 0.16 | 0.15 | 0.15 | 280.83 | 15.57 | 265.26 | |
| Water | 19164.0 | 5.67 | | 19676.0 | 17838.84 | 17838.84 | 139.18 | 120.79 | 18.39 | 18.38 |
| Ethylene glycol | 116.52 | | | 128.52 | 116.52 | 116.52 | 0.01 | 0.01 | | |
| Others | | | | | | | | | | |
| Flow rate (kg-mol/Hr) | 19578.64 | 22.50 | | 19804.68 | 17955.51 | 17955.51 | 423.87 | 136.37 | 287.50 | 18.38 |
| Pressure (kg/$cm^2$abs) | 6 | 3.0 | 3.2 | 1.073 | 5 | 5 | 3 | 6 | 2.95 | 3 |
| Temperature (°C.) | 52.5 | 91.6 | 135 | 101.3 | 59.2 | 40.7 | 89.2 | 136.37 | 60 | 135 |
| Steam (kg/Hr) | | | 8735 | | | | | | | |
| Cooling water ($m^3$/Hr) | | | | | | | | | | |

TABLE 9-continued

| Component part | Unit (Kg mol/Hr) | | | | | | |
|---|---|---|---|---|---|---|---|
| | 638 | 639 | 648 | 649 | 657 | 667 | 686 |
| Inert gas | | 0.28 | | | | | |
| Carbon dioxide | 1.31 | 2.26 | 1.31 | | | | |
| Ethylene oxide | 252.22 | 13.04 | 3.3 | 248.92 | 243.93 | 4.99 | |
| Water | 0.01 | | | 0.01 | | 0.01 | 1449.94 |
| Ethylene glycol | | | | | | | |
| Others | | | | | | | |
| Flow rate (kg-mol/Hr) | 253.54 | 15.58 | 4.61 | 248.93 | 243.93 | 5.00 | 1449.94 |
| Pressure (kg/cm²abs) | 4.0 | 2.9 | 3.5 | 3.6 | 2.5 | 2.9 | 1.073 |
| Temperature (°C.) | 34.1 | 34 | 35 | 46.7 | 35 | 39.7 | 101.3 |
| Steam (kg/Hr) | | | | | | | |
| Cooling water (m³/Hr) | | | | | | | |

Pressure of the top of the ethylene oxide stripping tower: 3.0 kg/cm² ᵃ Amount of the bottom liquid of the ethylene oxide stripping tower to be flashed: 26128 kg/Hr

TABLE 10

| Component part | Unit (Kg mol/Hr) | | | | | | | | | |
|---|---|---|---|---|---|---|---|---|---|---|
| | 605 | 609 | 613 | 616a | 616b | 616c | 623 | 627 | 628 | 632 |
| Inert gas | 4.97 | 4.46 | | | | | 0.51 | | 0.51 | |
| Carbon dioxide | 9.41 | 4.10 | | | | | 5.31 | | 5.31 | |
| Ethylene oxide | 283.74 | 2.36 | | 0.15 | 0.14 | 0.14 | 278.16 | 2.93 | 275.23 | |
| Water | 19164.0 | 1.45 | | 19636.0 | 18674.39 | 18674.39 | 118.44 | 10.09 | 48.35 | 48.34 |
| Ethylene glycol | 116.52 | | | 122.52 | 116.52 | 116.52 | | | | |
| Others | | | | | | | | | | |
| Flow rate (kg-mol/Hr) | 19578.64 | 12.37 | | 19758.67 | 18791.05 | 18791.05 | 402.42 | 13.02 | 329.40 | 48.34 |
| Pressure (kg/cm²abs) | 6 | 3 | 3.2 | 0.519 | 5 | 5 | 1.4 | 6 | 1.35 | 1.4 |
| Temperature (°C.) | 52.5 | 72.3 | 135 | 81.9 | 61.7 | 40.4 | 76.6 | 60.1 | 60 | 108.8 |
| Steam (kg/Hr) | | | 9079 | | | | | | | |
| Cooling water (m³/Hr) | | | | | | | | | | |

| Component part | Unit (Kg mol/Hr) | | | | | | |
|---|---|---|---|---|---|---|---|
| | 638 | 639 | 648 | 649 | 657 | 667 | 686 |
| Inert gas | | 0.51 | | | | | |
| Carbon dioxide | 1.52 | 3.79 | 1.52 | | | | |
| Ethylene oxide | 263.89 | 11.34 | 3.85 | 260.04 | 255.05 | 4.99 | |
| Water | 0.01 | | | 0.01 | | 0.01 | 1169.70 |
| Ethylene glycol | | | | | | | |
| Others | | | | | | | |
| Flow rate (kg-mol/Hr) | 265.42 | 15.64 | 5.37 | 260.05 | 255.05 | 5.00 | 1169.70 |
| Pressure (kg/cm²abs) | 1.4 | 1.3 | 1.3 | 1.4 | 2.5 | 2.9 | 0.519 |
| Temperature (°C.) | 8 | 8 | 8 | 18 | 35 | 39.7 | 81.9 |
| Steam (kg/Hr) | | | | | | | |
| Cooling water (m³/Hr) | | | | | | | |

Pressure of the top of the ethylene oxide stripping tower: 1.4 kg/cm² ᵃ Amount of the bottom liquid of the ethylene oxide stripping tower to be flashed: 21078 kg/Hr

TABLE 11

| Component part | Unit (Kg mol/Hr) | | | | | | | | | |
|---|---|---|---|---|---|---|---|---|---|---|
| | 605 | 609 | 613 | 616a | 616b | 616c | 623 | 627 | 628 | 632 |
| Inert gas | 4.97 | 4.69 | | | | | 0.28 | | 0.28 | |
| Carbon dioxide | 9.41 | 5.84 | | | | | 3.57 | | 3.57 | |
| Ethylene oxide | 283.74 | 6.30 | | 0.16 | 0.15 | 0.15 | 280.83 | 15.55 | 265.28 | |
| Water | 19164.0 | 5.67 | | 19688.0 | 17849.72 | 17849.72 | 139.06 | 120.66 | 18.40 | 18.38 |
| Ethylene glycol | 116.52 | | | 128.52 | 116.52 | 116.52 | 0.01 | 0.01 | | |
| Others | | | | | | | | | | |
| Flow rate (kg-mol/Hr) | 19578.64 | 22.50 | | 19816.68 | 17966.39 | 17966.39 | 423.75 | 136.22 | 287.53 | 18.38 |
| Pressure (kg/cm²abs) | | 3 | 3.2 | 1.073 | 5 | 5 | 3.0 | 6 | 2.95 | 3.0 |
| Temperature (°C.) | | 91.56 | 135 | 101.3 | 59.2 | 40.8 | 99.2 | 60.1 | 60 | 133 |
| Steam (kg/Hr) | | | 9558 | | | | | | | |
| Cooling water (m³/Hr) | | | | | | | | | | |

| Component part | Unit (Kg mol/Hr) | | | | | | |
|---|---|---|---|---|---|---|---|
| | 638 | 639 | 648 | 649 | 657 | 667 | 686 |

TABLE 11-continued

| | Unit (Kg mol/Hr) | | | | | | |
|---|---|---|---|---|---|---|---|
| Inert gas | | 0.28 | | | | | |
| Carbon dioxide | 1.30 | 2.27 | 1.30 | | | | |
| Ethylene oxide | 252.24 | 13.04 | 3.30 | 248.94 | 243.96 | 4.98 | |
| Water | 0.02 | | | 0.02 | | 0.02 | 1405.8 |
| Ethylene glycol | | | | | | | |
| Others | | | | - | | | |
| Flow rate (kg-mol/Hr) | 253.56 | 15.59 | 4.60 | 248.96 | 243.96 | 5.00 | 1405.8 |
| Pressure (kg/cm²abs) | 4 | 2.9 | 3.5 | 3.6 | 2.5 | 2.9 | 1.073 |
| Temperature (°C.) | 34.1 | 34 | 35 | 46.7 | 35 | 39.7 | 101.3 |
| Steam (kg/Hr) | | | | | | | |
| Cooling water (m³/Hr) | | | | | | | |

Pressure of the top of the ethylene oxide stripping tower: 3.0 kg/cm² a Amount of the bottom liquid of the ethylene oxide stripping tower to be flashed: 25332 kg/Hr

TABLE 12

| | Composition (% by weight) | | | | | | | | | | | | | | |
|---|---|---|---|---|---|---|---|---|---|---|---|---|---|---|---|
| Component part | 7 | 9 | 10 | 13 | 16 | 18 | 19 | 23 | 25 | 26 | 28 | 49 | 56 | 58 | 59 |
| Inert gas | 0.06 | 24.22 | | | | | | | | | | | | | |
| Carbon dioxide | 0.11 | 30.10 | 0.04 | | | | | 0.67 | | | 1.27 | | | | |
| Ethylene oxide | 2.73 | 30.34 | 2.60 | | | | | 52.95 | | | 95.75 | 99.97 | ≃100 | ≃100 | |
| Water | 88.46 | 15.34 | 88.62 | | 91.00 | | | 46.34 | | | 2.98 | 0.01 | | | |
| Ethylene glycol | 8.64 | | 8.74 | | 9.00 | | | 0.04 | | | | | | | |
| Others | | | | | | | | | | | | 0.02 | | | |
| Flow rate (kg/Hr) | 308100 | 810 | 307290 | | 295600 | | | 15500 | | | 8200 | 7600 | 23400 | 7594 | |
| Pressure (kg/cm²G) | 3.4 | 3.4 | 3.4 | 2.2 | 3 | 3 | 3 | 0.4 | 3 | 3 | 0.3 | 5 | 3.5 | 3.5 | 2.2 |
| Temperature (°C.) | 105.5 | 104.7 | 104.7 | 135 | 56.5 | 25 | 40 | 99.6 | 25 | 35 | 45 | 64 | 35 | 35 | 135 |
| Steam (kg/Hr) | | | | 14900 | | | | | | | | | | | 8000 |
| Cooling water (m³/Hr) | | | | | | 510 | 510 | | 410 | 410 | | | | | |

TABLE 13

| | Composition (% by Weight) | | | | | | | | | | | | | | |
|---|---|---|---|---|---|---|---|---|---|---|---|---|---|---|---|
| Component part | 407 | 409 | 410 | 413 | 423 | 462 | 463 | 428 | 449 | 456 | 457 | 486 | 416b | 442 | 416cl |
| Inert gas | 0.07 | 39.72 | | | | | | | | | | | | | |
| Carbon dioxide | 0.11 | 36.52 | 0.06 | | 1.49 | | | 2.02 | | | | | | | |
| Ethylene oxide | 2.66 | 17.21 | 2.64 | | 73.21 | | | 94.19 | 99.97 | ≃100 | ≃100 | | | | |
| Water | 91.62 | 6.55 | 91.75 | | 25.30 | | | 3.79 | 0.01 | | | 99.91 | 94.28 | 94.28 | 94.28 |
| Ethylene glycol | 5.54 | | 5.55 | | | | | | | | | 0.09 | 5.72 | 5.72 | 5.72 |
| Others | | | | | | | | | 0.02 | | | | | | |
| Flow rate (kg/Hr) | 310900 | 510 | 310390 | | 11700 | | | 8600 | 7700 | 23700 | 7640 | 12800 | 298300 | 298300 | 298100 |
| Pressure (kg/cm²G) | 3.4 | 3.4 | 3.4 | 2.2 | 0.4 | 3.0 | 3.0 | 0.3 | 2.0 | 1.8 | 1.8 | −0.35 | 3 | 3 | 3 |
| Temperature (°C.) | 82.7 | 82.6 | 82.6 | 135 | 87.0 | 25 | 35 | 50 | 42 | 35 | 35 | 87.5 | 56.5 | 53.6 | 45.5 |
| Steam (kg/Hr) | | | | 7500 | | | | | | | 4700 | | | | |
| Cooling water (m³/Hr) | | | | | | 14 | 14 | | | | | | | | |

By the method of this invention, since the vapor which is generated when the bottom liquid of the ethylene oxide stripper is flashed is separated from the flash drum, compressed by compression means to a pressure slightly higher than the bottom pressure of the ethylene oxide stripper, and introduced to the vapor-phase part in the bottom of the ethylene oxide stripper, there is manifested an effect of generously decreasing the amount of heat required for heating the ethylene oxide stripper. Further, by recovering heat from the liquid of the ethylene oxide stripper by means of a heat pump and utilizing the recovered heat as a heat source for the ethylene oxide refiner, saving of the energy consumed by the ethylene oxide refiner can be attained at the same time. Furthermore, by utilizing the liquid remaining after the flash treatment of the bottom liquid of the ethylene oxide stripper as heat sources for the ethylene oxide refiner and the light ends stripper, saving of the energy consumed by the ethylene oxide refiner and the light ends stripper can be accomplished. Moreover, by carrying out this method, there is manifested an effect of decreasing the thermal loads of the cooling water used in cooling the absorbent liquid forwarded to the ethylene oxide absorber and the condenser for the vapor of the top of the ethylene oxide stripper.

What is claimed is:

1. In a method for the recovery of ethylene oxide, comprising the steps of introducing the gas resulting from catalytic gas-phase oxidation of ethylene with a molecular oxygen-containing gas said resultant gas containing ethylene oxide into an absorber and leading said gas into counterflow contact therein with an aqueous absorbent liquid, recycling part of the residual gas emanating from the top of said absorber to the reactor or said oxidation step of ethylene, introducing an ethylene oxide-containing bottom liquid of said absorber to an ethylene oxide stripper, heating the bottom of said ethylene oxide stripper with a heating medium, causing said stripper to liberate a volatile component containing ethylene oxide as a volatile fraction via the top thereof, forwarding said volatile component to a condenser to condense therein a condensate containing ethylene oxide and water, leaving uncondensed vapour, recycling the condensate to the said stripper and passing the said uncondensed vapour to a dehydrator to separate water therefrom, separating the volatile components from said dehydrator in a light ends stripper to yield ethylene oxide, subjecting the ethylene oxide produced to purification in an ethylene oxide refiner, and forwarding part of the liquid withdrawn from the bottom of said stripper to said absorber to be used as an absorbent liquid again, the improvement comprising introducing the volatile component from said stripper having 0.3 to 0.6 Kg/cm$^2$ G of a top pressure and 85° to 120° C. of a temperature to a heating zone of said ethylene oxide refiner, then passing it into a condenser to form a condensate, and recirculating said condensate to the said ethylene oxide stripper, while circulating the uncondensed vapour therefrom to a dehydrator, subjecting the aqueous liquid having not more than 0.5 ppm of ethylene oxide content withdrawn from the bottom of said stripper to a flashing treatment in a flash tank thereby separating said liquid into a vapour-phase part and an aqueous liquid phase part, introducing said vapour-phase part in a compressed state into the bottom of said stripper;

introducing said liquid phase as a heat source into a heating means for said ethylene oxide refiner after preheating a liquid which is fed from the bottom of said ethylene oxide absorber to said ethylene oxide stripper, and then recycling said aqueous liquid-phase part into said absorber as an absorbent liquid for use in said absorber.

2. A method according to claim 1, wherein said liquid-phase part is caused by a heat exchanger to exchange heat with the bottom liquid of said absorber, then said absorbent liquid is caused by a heat pump to liberate thermal energy and generate steam, and said absorbent liquid cooled by said heat pump is further cooled and then circulated to said absorber.

3. A method according to claim 2, wherein said heat pump is operated so that when the bottom liquid of the ethylene oxide stripper which has liberated heat through exchange of heat with said absorbent liquid enters, at a temperature of 50° C. to 60° C., a refrigerant vaporizer, said bottom liquid has the temperature thereof lowered by 5° to 20° C. through vaporization of refrigerant.

4. A method according to claim 1, wherein said liquid-phase part is caused to exchange heat with an ethylene oxide-containing absorbent liquid for ethylene oxide, used as a heat source for an ethylene oxide refiner, cooled in cooler, and then circulated into said ethylene oxide absorber and used as an absorbent liquid therein.

5. A method according to claim 4, wherein said ethylene oxide refiner is a tray type distillation tower possessing a pressure drop of not more than 20 mmHg per theoretical step.

6. A method according to claim 4, wherein said ethylene oxide refiner is a packed type distillation tower possessing a pressure drop of not more than 10 mmHg per theoretical step.

7. In a method for the recovery of ethylene oxide, comprising the steps of introducing the gas resulting from catalytic gas-phase oxidation of ethylene with a molecular oxygen-containing gas said resultant gas containing ethylene oxide into an absorber and leading said gas into counterflow contact therein with an aqueous absorbent liquid, recycling part of the residual gas emanating from the top of said absorber to the reactor or said oxidation step of ethylene, introducing an ethylene oxide-containing bottom liquid of said absorber to an ethylene oxide stripper, heating the bottom of said ethylene oxide stripper with a heating medium, causing said stripper to liberate a volatile component containing ethylene oxide as a volatile fraction via the top thereof, forwarding said volatile component to a condenser to condense therein a condensate containing ethylene oxide and water, leaving uncondensed vapour, recycling the condensate to the said stripper and passing the said uncondensed vapour to a dehydrator to separate water therefrom, separating the volatile components from said dehydrator in a light ends stripper to yield ethylene oxide, subjecting the ethylene oxide produced to purification in an ethylene oxide refiner, and forwarding part of the liquid withdrawn from the bottom of said stripper to said absorber to be used as an absorbent liquid again, the improvement comprising introducing the volatile component from said stripper having 0.3 to 0.6 Kg/cm$^2$ G of a top pressure and 85° to 120° C. of a temperature to a heating zone of said ethylene oxide refiner, then passing it into a condenser to form a condensate, and recirculating said condensate to the said ethylene oxide stripper, while circulating the uncondensed vapour therefrom to a dehydrator, subjecting the aqueous liquid having not more than 5 ppm of ethylene oxide content withdrawn from the bottom of said stripper to a flashing treatment in a flash tank thereby separating said liquid into a vapour-phase part and an aqueous liquid phase part, introducing said vapour-phase part in a compressed state into the bottom of said stripper, introducing said liquid phase as a heat source into a heating means for said ethylene oxide refiner and then as a heat source introduced into a heating means for said light ends stripper after preheating a liquid which is fed from the bottom of said ethylene oxide absorber to said ethylene oxide stripper, and then recycling said aqueous liquid-phase part into said absorber as an absorbent liquid for use in said absorber.

8. A method according to claim 7, wherein said ethylene oxide refiner is a tray type distillation tower possessing a pressure drop of not more than 20 mmHg per theoretical step.

9. A method according to claim 7, wherein said ethylene oxide refiner is a packed type distillation tower possessing a pressure drop of not more than 10 mmHg per theoretical step.

10. A method according to claim 7, wherein said light ends stripper is a tray type separation tower possessing a pressure drop of not more than 20 mmHg per theoretical step.

11. A method according to claim 7, wherein said light ends stripper is a packed type separation tower possessing a pressure drop of not more than 10 mmHg per theoretical step.

12. A method according to claim 7, wherein the diffusate liberated through the top of said ethylene oxide stripper is used as a heat source for said ethylene oxide refiner.

13. In a method for the recovery of ethylene oxide, comprising the steps of introducing the gas resulting from catalytic gas-phase oxidation of ethylene with a molecular oxygen-containing gas said resultant gas containing ethylene oxide into an absorber and leading said gas into counterflow contact therein with an aqueous absorbent liquid,
   recycling part of the residual gas emanating from the top of said absorber to the reactor or said oxidation step of ethylene, introducing an ethylene oxide-containing bottom liquid of said absorber to an ethylene oxide stripper,
   heating the bottom of said ethylene oxide stripper with a heating medium,
   causing ethylene oxide as a volatile component containing ethylene oxide as a volatile fraction via the top thereof,
   forwarding said volatile component to a condenser to condense therein a condensate containing ethylene oxide and water,
   leaving uncondensed vapour,
   recycling the condensate to the said stripper and passing the said uncondensed vapour to a dehydrator to separate water therefrom,
   separating the volatile components from said dehydrator in a light ends stripper to yield ethylene oxide, and
   subjecting the ethylene oxide produced to purification in an ethylene oxide refiner, and
   forwarding part of the liquid withdrawn from the bottom of said stripper to said absorber to be used as an absorbent liquid again, the improvement comprising
   introducing the volatile component from said stripper having 0.3 to 0.6 Kg/cm$^2$ G of a top pressure and 85° to 120° C. of a temperature to a heating zone of said ethylene oxide refiner,
   then passing it into a condenser to form a condensate, and recirculating said condensate to the said ethylene oxide stripper, while circulating the uncondensed vapour thereform to a dehydrator,
   subjecting the aqueous liquid having not more than 0.5 ppm of ethylene oxide content withdrawn from the bottom of said stripper to a flashing treatment in a flash tank thereby separating said liquid into a vapour-phase part and an aqueous liquid phase part,
   introducing said vapour-phase part in a compressed state into the bottom of said stripper,
   introducing said liquid phase as a heat source into a heating means for said light ends stripper after preheating a liquid which is fed from the bottom of said ethylene oxide absorber to said ethylene oxide stripper, and then recycling said aqueous liquid-phase part into said absorber as an absorbent liquid for use in said absorber.

14. A method according to claim 13, wherein said light ends stripper is a tray type separation tower possessing a pressure drop of not more than 20 mmHg per theoretical step.

15. A method according to claim 13, wherein said light ends stripper is a packed type separation tower possessing a pressure drop of not more than 10 mmHg per theoretical step.

16. In a method for the recovery of ethylene oxide, comprising the steps of introducing the gas resulting from catalytic gas-phase oxidation of ethylene with a molecular oxygen-containing gas said resultant gas containing ethylene oxide into an absorber and leading said gas into counterflow contact therein with an aqueous absorbent liquid,
   recycling part of the residual gas emanating from the top of said absorber to the reactor or said oxidation step of ethylene, introducing an ethylene oxide-containing bottom liquid of said absorber to an ethylene oxide stripper,
   heating the bottom of said ethylene oxide stripper with a heating medium,
   causing said stripper to liberate a volatile component containing ethylene oxide as a volatile fraction via the top thereof,
   forwarding said volatile component to a condensor to condense therein a condensate containing ethylene oxide and water,
   leaving uncondensed vapour,
   recycling the condensate to the said stripper and passing the said uncondensed vapour to a dehydrator to separate water therefrom,
   separating the volatile components from said dehydrator in a light ends stripper to yield ethylene oxide,
   subjecting the ethylene oxide produced to purification in an ethylene oxide refiner, and
   forwarding part of the liquid withdrawn from the bottom of said stripper to said absorber to be used as an absorbent liquid again, the improvement comprising
   introducing the volatile component from said stripper having 0.3 to 0.6 Kg/cm$^2$ G of a top pressure and 85° to 120° C. of a temperature to a heating zone of said ethylene oxide refiner,
   then passing it into a condenser to form a condensate, and recirculating said condensate to the said ethylene oxide stripper, while circulating the uncondensed vapour therefrom to a dehydrator,
   subjecting the aqueous liquid withdrawn having not more than 0.5 ppm of ethylene oxide content from the bottom of said stripper to a flashing treatment in a flash tank thereby separating said liquid into a vapour-phase part and an aqueous liquid phase part,
   introducing said vapour-phase part in a compressed state into the bottom of said stripper,
   simultaneously introducing said liquid phase as a heat source into a heating means for said ethylene oxide refiner and into a heating means for said light ends stripper after preheating a liquid which is fed from the bottom of said ethylene oxide absorber to said ethylene oxide stripper, and then recycling said aqueous liquid-phase part into said absorber as an absorbent liquid for use in said absorber.

17. A method according to claim 16, wherein said ethylene oxide refiner is a tray type distillation tower possessing a pressure drop of not more than 20 mmHg per theoretical step.

18. A method according to claim 16, wherein said ethylene oxide refiner is a packed type distillation tower possessing a pressure drop of not more than 10 mmHg per theoretical step.

19. A method according to claim 16, wherein said light ends stripper is a tray type separation tower possessing a pressure drop of not more than 20 mmHg per theoretical step.

20. A method according to claim 16, wherein said light ends stripper is a packed type separation tower possessing a pressure drop of not more than 10 mmHg per theoretical step.

21. A method according to claim 16, wherein the diffusate liberated through the top of said ethylene oxide stripper is used as a heat source for said ethylene oxide refiner.

* * * * *